(12) United States Patent
Gunnsteinsson et al.

(10) Patent No.: US 12,156,825 B2
(45) Date of Patent: Dec. 3, 2024

(54) ORTHOPEDIC WALKER

(71) Applicant: OSSUR ICELAND EHF, Reykjavik (IS)

(72) Inventors: Larus Gunnsteinsson, Reykjavik (IS); Gudni Ingimarsson, Reykjavik (IS); Bjorn Omarsson, Reykjavik (IS); Sindri Pall Sigurdsson, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 88 days.

(21) Appl. No.: 16/266,925

(22) Filed: Feb. 4, 2019

(65) Prior Publication Data
US 2019/0240057 A1    Aug. 8, 2019

Related U.S. Application Data

(60) Provisional application No. 62/625,527, filed on Feb. 2, 2018.

(51) Int. Cl.
*A61F 5/01*    (2006.01)
*B29C 45/14*    (2006.01)

(52) U.S. Cl.
CPC .......... *A61F 5/0195* (2013.01); *A61F 5/0111* (2013.01); *B29C 45/14008* (2013.01); *B29C 45/14467* (2013.01)

(58) Field of Classification Search
CPC .... A61F 5/0111; A61F 5/0195; A61F 5/0113; A61F 5/0127; A61F 5/0585; B29C 45/14008; B29C 45/14467

(Continued)

(56) References Cited

U.S. PATENT DOCUMENTS 346,606 A   *   8/1886   Pugsley ................ A61F 13/066
                                                        602/65
975,576 A     11/1910   Sexton
(Continued)

FOREIGN PATENT DOCUMENTS

| CN | 101711141 A | 5/2010 |
|---|---|---|
| CN | 102026592 A | 4/2011 |
| DE | 23 416 58 A1 | 3/1974 |
| DE | 32 287 53 A1 | 2/1984 |
| DE | 9314920 U1 | 3/1994 |
| EP | 0 095 396 A1 | 11/1983 |
| EP | 0 201 051 A1 | 11/1986 |
| EP | 0770368 A1 | 5/1997 |
| EP | 1238640 A1 | 9/2002 |

(Continued)

OTHER PUBLICATIONS

FoamFactory, Polyethylene Foam: Its Uses, Characteristics, and Varieties, Nov. 9, 2011, https://www.foambymail.com/blog/polyethylene-foam-its-uses-characteristics-and-varieties/#:~:text=Polyethylene%20is%20closed%2Dcell%20foam,present%20in%20open%2Dcell%20foams (Year: 2011).*

(Continued)

*Primary Examiner* — Ophelia A Hawthorne
*Assistant Examiner* — Michael Milo
(74) *Attorney, Agent, or Firm* — Workman Nydegger

(57) ABSTRACT

An orthopedic walker or walking boot has a body formed from at least one polymeric material. The body defines an upper receiving section, a lower receiving section, and a footbed. The upper receiving section includes first and second portions divided by a median plane of the orthopedic walker, and are arranged to individually articulate about or from the median plane to expand or retract a variable distance between the first and second portions of the upper receiving section along one of anterior or posterior sides of the body. The body may consist of the upper receiving section, the lower receiving section, and the footbed as a continuous structure formed unitarily from the expanded thermoplastic.

20 Claims, 18 Drawing Sheets

(58) Field of Classification Search
USPC .................................................. 602/23, 27
See application file for complete search history.

(56) References Cited

U.S. PATENT DOCUMENTS

| | | |
|---|---|---|
| 1,012,017 A | 12/1911 | Salt |
| 2,200,849 A | 5/1940 | Margolin |
| 2,236,367 A | 3/1941 | Gruber |
| 2,292,297 A | 8/1942 | Sherlock |
| 2,444,640 A | 7/1948 | Epstein |
| 2,868,191 A | 1/1959 | Juhasz |
| 2,885,797 A | 5/1959 | Chrencik |
| 2,888,016 A | 5/1959 | De Lamater |
| 2,909,854 A | 10/1959 | Edelstein |
| 2,913,837 A | 11/1959 | Geuder |
| 2,917,844 A | 12/1959 | Scholl |
| 2,928,193 A | 3/1960 | Kristan |
| 2,979,835 A | 4/1961 | Scholl |
| 2,979,836 A | 4/1961 | Scholl |
| 3,270,358 A | 9/1966 | Milner |
| 3,464,126 A | 9/1969 | Sarkissian |
| 3,548,420 A | 12/1970 | Spence |
| 3,580,248 A | 5/1971 | Larson |
| 3,681,860 A | 8/1972 | Bidegain |
| 3,685,176 A | 8/1972 | Rudy |
| 3,730,169 A | 5/1973 | Fiber |
| 3,735,758 A | 5/1973 | Novotney |
| 3,760,056 A | 9/1973 | Rudy |
| 3,786,805 A | 1/1974 | Tourin |
| 3,792,537 A | 2/1974 | Plank et al. |
| 3,814,088 A | 6/1974 | Raymond |
| 3,834,377 A | 9/1974 | Lebold |
| 3,859,740 A | 1/1975 | Kemp |
| 3,922,800 A | 12/1975 | Miller et al. |
| 3,955,565 A | 5/1976 | Johnson, Jr. |
| 4,045,888 A | 9/1977 | Oxenberg |
| 4,057,056 A | 11/1977 | Payton |
| 4,095,353 A | 6/1978 | Foldes |
| 4,100,686 A | 7/1978 | Sgarlato et al. |
| 4,142,307 A | 3/1979 | Martin |
| 4,177,583 A | 12/1979 | Chapman |
| 4,184,273 A | 1/1980 | Boyer et al. |
| 4,217,706 A | 8/1980 | Vartanian |
| 4,217,893 A | 8/1980 | Payton |
| 4,232,459 A | 11/1980 | Vaccari |
| 4,237,626 A | 12/1980 | Brown |
| 4,267,649 A | 5/1981 | Smith |
| 4,300,294 A | 11/1981 | Riecken |
| 4,333,248 A | 6/1982 | Samuels |
| 4,370,818 A | 2/1983 | Simoglou |
| 4,408,402 A | 10/1983 | Looney |
| 4,414,965 A | 11/1983 | Mauldin et al. |
| D272,281 S | 1/1984 | Alush |
| 4,446,856 A | 5/1984 | Jordan |
| 4,494,536 A | 1/1985 | Latenser |
| 4,505,269 A | 3/1985 | Davies et al. |
| 4,550,721 A | 11/1985 | Michel |
| 4,565,017 A | 1/1986 | Ottieri |
| 4,571,853 A | 2/1986 | Medrano |
| 4,572,169 A | 2/1986 | Mauldin et al. |
| 4,587,962 A | 5/1986 | Greene et al. |
| 4,598,484 A | 7/1986 | Ma |
| 4,599,811 A | 7/1986 | Rousseau |
| 4,608,768 A | 9/1986 | Cavanagh |
| 4,620,378 A | 11/1986 | Sartor |
| 4,633,598 A | 1/1987 | Moronaga et al. |
| 4,633,599 A | 1/1987 | Morell et al. |
| 4,633,877 A | 1/1987 | Pendergast |
| 4,638,794 A * | 1/1987 | Grisar .................. A61F 5/0111 602/27 |
| 4,660,300 A | 4/1987 | Morell et al. |
| 4,669,202 A | 6/1987 | Ottieri |
| 4,674,204 A | 6/1987 | Sullivan et al. |
| 4,674,205 A | 6/1987 | Anger |
| 4,677,767 A | 7/1987 | Darby |
| 4,680,878 A | 7/1987 | Pozzobon et al. |
| 4,689,898 A | 9/1987 | Fahey |
| 4,719,710 A | 1/1988 | Pozzobon |
| 4,727,661 A | 3/1988 | Kuhn |
| 4,741,115 A | 5/1988 | Pozzobon |
| 4,748,726 A | 6/1988 | Schoch |
| 4,760,653 A | 8/1988 | Baggio |
| 4,771,768 A | 9/1988 | Crispin |
| 4,773,170 A | 9/1988 | Moore et al. |
| 4,793,078 A | 12/1988 | Andrews |
| D299,787 S | 2/1989 | Bates |
| 4,805,321 A | 2/1989 | Tonkel |
| 4,805,601 A | 2/1989 | Eischen, Sr. |
| 4,811,504 A | 3/1989 | Bunke |
| 4,869,001 A | 9/1989 | Brown |
| 4,872,273 A | 10/1989 | Smeed |
| 4,879,822 A | 11/1989 | Hayes |
| 4,893,418 A | 1/1990 | Ogden |
| 4,934,355 A | 6/1990 | Porcelli |
| 4,947,838 A | 8/1990 | Giannetti |
| 4,974,583 A | 12/1990 | Freitas |
| 5,056,509 A | 10/1991 | Swearington |
| 5,065,481 A | 11/1991 | Walkhoff |
| 5,065,531 A | 11/1991 | Prestridge |
| 5,078,128 A | 1/1992 | Grim et al. |
| 5,123,180 A | 6/1992 | Nannig et al. |
| 5,125,400 A | 6/1992 | Johnson, Jr. |
| D329,527 S | 9/1992 | Cohen |
| 5,143,058 A | 9/1992 | Luber et al. |
| D330,109 S | 10/1992 | Hatfield |
| 5,152,038 A | 10/1992 | Schoch |
| 5,154,682 A | 10/1992 | Kellerman |
| 5,154,695 A | 10/1992 | Farris et al. |
| 5,157,813 A | 10/1992 | Carroll |
| 5,176,623 A | 1/1993 | Stetman et al. |
| 5,176,624 A | 1/1993 | Kuehnreich |
| 5,183,036 A | 2/1993 | Spademan |
| 5,197,942 A | 3/1993 | Brady |
| D334,646 S | 4/1993 | Dissinger |
| D337,876 S | 8/1993 | Kilbey |
| 5,233,767 A | 8/1993 | Kramer |
| 5,242,379 A | 9/1993 | Harris et al. |
| 5,257,470 A | 11/1993 | Auger et al. |
| 5,277,695 A | 1/1994 | Johnson, Jr. et al. |
| D344,589 S | 2/1994 | Kilbey |
| 5,288,286 A | 2/1994 | Davis et al. |
| 5,325,613 A | 7/1994 | Sussmann |
| 5,329,705 A | 7/1994 | Grim et al. |
| 5,352,189 A | 10/1994 | Schumann et al. |
| D352,191 S | 11/1994 | Zorian |
| D352,784 S | 11/1994 | Cohen et al. |
| 5,359,791 A | 11/1994 | Prahl et al. |
| 5,368,549 A | 11/1994 | McVicker |
| 5,368,551 A | 11/1994 | Zuckerman |
| 5,370,133 A | 12/1994 | Darby et al. |
| 5,378,223 A | 1/1995 | Grim et al. |
| 5,399,152 A | 3/1995 | Habermeyer et al. |
| 5,407,421 A | 4/1995 | Goldsmith |
| 5,425,701 A | 6/1995 | Oster et al. |
| 5,426,872 A | 6/1995 | Hayes |
| 5,429,377 A | 7/1995 | Duer |
| 5,429,588 A | 7/1995 | Young et al. |
| 5,433,695 A | 7/1995 | Drennan |
| 5,435,009 A | 7/1995 | Schild et al. |
| 5,438,768 A | 8/1995 | Bauerfeind |
| 5,441,015 A | 8/1995 | Farley |
| D363,780 S | 10/1995 | Darby et al. |
| 5,464,385 A | 11/1995 | Grim |
| 5,477,593 A | 12/1995 | Leick |
| D365,919 S | 1/1996 | Chen |
| 5,483,757 A | 1/1996 | Frykberg |
| 5,496,263 A * | 3/1996 | Fuller, II ................ A61F 5/0127 602/23 |
| 5,548,848 A | 8/1996 | Huybrechts |
| D373,548 S | 9/1996 | Losi, II |
| 5,558,627 A | 9/1996 | Singer et al. |
| D375,191 S | 11/1996 | Tonkel et al. |
| 5,573,501 A | 11/1996 | Ruscito et al. |
| 5,577,998 A | 11/1996 | Johnson, Jr. et al. |

(56) References Cited

U.S. PATENT DOCUMENTS

| | | |
|---|---|---|
| D376,429 S | 12/1996 | Antar |
| 5,617,650 A | 4/1997 | Grim |
| D379,258 S | 5/1997 | Cheng |
| 5,641,322 A | 6/1997 | Silver et al. |
| 5,647,104 A | 7/1997 | James |
| 5,656,226 A | 8/1997 | McVicker |
| D383,250 S | 9/1997 | Amico |
| D384,746 S | 10/1997 | Varn |
| D390,345 S | 2/1998 | Aird et al. |
| 5,717,996 A | 2/1998 | Feldmann |
| D391,748 S | 3/1998 | Koh |
| 5,761,834 A | 6/1998 | Grim et al. |
| 5,778,563 A | 7/1998 | Ahlbaumer |
| 5,778,565 A | 7/1998 | Holt et al. |
| 5,797,862 A | 8/1998 | Lamont |
| D398,142 S | 9/1998 | Benoit |
| D398,439 S | 9/1998 | McDonald |
| 5,819,378 A | 10/1998 | Doyle |
| 5,827,210 A | 10/1998 | Antar et al. |
| 5,827,211 A | 10/1998 | Sellinger |
| D401,042 S | 11/1998 | Davis |
| 5,833,639 A | 11/1998 | Nunes et al. |
| 5,836,902 A | 11/1998 | Gray |
| 5,846,063 A | 12/1998 | Lakic |
| 5,853,380 A | 12/1998 | Miller |
| 5,857,987 A | 1/1999 | Habermeyer |
| D404,895 S | 2/1999 | Rosato |
| 5,868,690 A | 2/1999 | Eischen, Sr. |
| 5,913,841 A | 6/1999 | Lamont |
| 5,934,599 A | 8/1999 | Hammerslag |
| 5,951,504 A | 9/1999 | Iglesias et al. |
| 5,961,477 A | 10/1999 | Turtzo |
| 5,993,404 A | 11/1999 | McNiel |
| 6,000,148 A | 12/1999 | Cretinon |
| D418,967 S | 1/2000 | Stengel |
| 6,021,780 A | 2/2000 | Darby |
| 6,027,468 A | 2/2000 | Pick |
| 6,044,578 A | 4/2000 | Kelz |
| 6,098,315 A | 8/2000 | Hoffmann, III |
| 6,131,195 A | 10/2000 | Foreman |
| 6,202,953 B1 | 3/2001 | Hammerslag |
| 6,205,685 B1 | 3/2001 | Kellerman |
| D440,754 S | 4/2001 | Bathum |
| 6,228,044 B1 | 5/2001 | Jensen et al. |
| 6,267,742 B1 | 7/2001 | Krivosha et al. |
| RE37,338 E | 8/2001 | McVicker |
| 6,283,932 B1 | 9/2001 | Münch et al. |
| 6,289,558 B1 | 9/2001 | Hammerslag |
| 6,334,854 B1 * | 1/2002 | Davis .................. A61F 5/0111 602/65 |
| 6,338,768 B1 | 1/2002 | Chi |
| 6,361,514 B1 | 3/2002 | Brown et al. |
| 6,377,178 B1 | 4/2002 | Detoro et al. |
| 6,409,691 B1 | 6/2002 | Dakin et al. |
| D461,936 S | 8/2002 | Fiorini et al. |
| 6,432,073 B2 | 8/2002 | Pior et al. |
| D467,708 S | 12/2002 | Portzline |
| 6,517,505 B1 * | 2/2003 | Veldman .............. A61F 5/0111 602/5 |
| D473,654 S | 4/2003 | Iglesias et al. |
| D473,704 S | 4/2003 | Wilson |
| 6,572,571 B2 | 6/2003 | Lowe |
| D476,799 S | 7/2003 | Fuerst |
| 6,589,194 B1 | 7/2003 | Calderon et al. |
| 6,682,497 B2 | 1/2004 | Jensen et al. |
| 6,755,798 B2 | 6/2004 | McCarthy et al. |
| 6,792,699 B2 | 9/2004 | Long et al. |
| D500,855 S | 1/2005 | Pick et al. |
| 6,866,043 B1 | 3/2005 | Davis |
| D504,005 S | 4/2005 | Schoenborn et al. |
| D505,727 S | 5/2005 | Krahner et al. |
| 6,945,944 B2 | 9/2005 | Kuiper et al. |
| 6,976,972 B2 | 12/2005 | Bradshaw |
| 6,991,613 B2 | 1/2006 | Sensabaugh |
| D517,306 S | 3/2006 | Hoeft |
| 7,010,823 B2 | 3/2006 | Baek |
| 7,018,351 B1 | 3/2006 | Iglesias et al. |
| D523,217 S | 6/2006 | Matis et al. |
| D528,214 S | 9/2006 | Binet |
| 7,198,610 B2 | 4/2007 | Ingimundarson et al. |
| 7,281,341 B2 | 10/2007 | Reagan et al. |
| 7,288,076 B2 | 10/2007 | Grim et al. |
| D554,835 S | 11/2007 | Peydro |
| D555,291 S | 11/2007 | Danzo |
| D555,343 S | 11/2007 | Bettencourt |
| 7,303,538 B2 | 12/2007 | Grim et al. |
| 7,311,686 B1 | 12/2007 | Iglesias et al. |
| D559,988 S * | 1/2008 | Buethorn .................. D24/190 |
| 7,354,411 B2 | 4/2008 | Perry et al. |
| RE40,363 E | 6/2008 | Grim et al. |
| 7,384,584 B2 | 6/2008 | Jerome et al. |
| D575,039 S | 8/2008 | Amado et al. |
| D576,781 S | 9/2008 | Chang et al. |
| 7,418,755 B2 | 9/2008 | Bledsoe et al. |
| 7,455,651 B2 * | 11/2008 | Mollica .................. A61F 13/066 128/845 |
| D583,544 S | 12/2008 | Fuerst |
| D583,956 S | 12/2008 | Chang et al. |
| 7,493,706 B2 | 2/2009 | Cho et al. |
| 7,524,295 B1 | 4/2009 | Peters et al. |
| D592,755 S | 5/2009 | Chang et al. |
| D592,756 S | 5/2009 | Chang et al. |
| D594,368 S | 6/2009 | Butler |
| D596,301 S | 7/2009 | Campos et al. |
| D596,386 S | 7/2009 | Brambilla |
| 7,591,050 B2 | 9/2009 | Hammerslag |
| D603,155 S | 11/2009 | Della Valle et al. |
| D614,775 S | 4/2010 | Snively |
| D615,285 S | 5/2010 | Martin |
| D616,556 S | 5/2010 | Hu |
| 7,717,869 B2 | 5/2010 | Eischen, Sr. |
| 7,727,174 B2 | 6/2010 | Chang et al. |
| D622,494 S | 8/2010 | Warren |
| 7,838,717 B2 | 11/2010 | Haggstrom et al. |
| D634,438 S | 3/2011 | Hu |
| D634,852 S | 3/2011 | Hu |
| D636,157 S | 4/2011 | Nascimento |
| D636,159 S | 4/2011 | Petrie |
| 7,964,766 B2 | 6/2011 | Blott et al. |
| D642,363 S | 8/2011 | Rajmohan et al. |
| D642,775 S | 8/2011 | Raysse |
| 8,002,724 B2 | 8/2011 | Hu et al. |
| 8,012,112 B2 | 9/2011 | Barberio |
| 8,021,347 B2 | 9/2011 | Vitaris et al. |
| D648,113 S | 11/2011 | Chang |
| RE43,063 E | 1/2012 | Kim |
| D651,381 S | 1/2012 | Simms |
| 8,158,844 B2 | 4/2012 | McNeil |
| D661,887 S | 6/2012 | Petrie |
| 8,308,705 B2 | 11/2012 | Lin et al. |
| 8,313,449 B2 | 11/2012 | Hardman et al. |
| D675,421 S | 2/2013 | Petrie |
| D677,866 S | 3/2013 | Vestuti et al. |
| D680,728 S | 4/2013 | Stryjak |
| D682,517 S | 5/2013 | Taylor |
| D683,214 S | 5/2013 | McAdam |
| D684,760 S | 6/2013 | Williams, Jr. |
| 8,506,510 B2 | 8/2013 | Hu et al. |
| D689,677 S | 9/2013 | Bathum et al. |
| 8,574,181 B2 | 11/2013 | Bird et al. |
| D696,499 S | 12/2013 | Lehtinen |
| D696,785 S | 12/2013 | Weaver, II et al. |
| D698,074 S | 1/2014 | Hargreaves |
| D698,338 S | 1/2014 | Ingham et al. |
| D700,404 S | 2/2014 | Niefer |
| D701,032 S | 3/2014 | Leleu |
| D701,033 S | 3/2014 | Leleu |
| D703,335 S | 4/2014 | Bird et al. |
| D709,277 S | 7/2014 | Takenaka |
| D712,639 S | 9/2014 | Spring |
| D714,042 S | 9/2014 | Petrie |
| 9,003,677 B2 | 4/2015 | Goodsmith et al. |
| D729,393 S | 5/2015 | Dunn et al. |
| D740,896 S | 10/2015 | Halper, Jr. |

(56) References Cited

U.S. PATENT DOCUMENTS

| | | | |
|---|---|---|---|
| D742,017 S | 10/2015 | Dunn et al. | |
| D744,111 S | 11/2015 | Dunn et al. | |
| 9,220,621 B2 | 12/2015 | Hu et al. | |
| 9,220,622 B2 | 12/2015 | Ingimundarson et al. | |
| 9,248,042 B2 | 2/2016 | Lopez et al. | |
| 9,333,106 B2 | 5/2016 | Hu et al. | |
| 9,468,553 B2 | 10/2016 | Hu et al. | |
| 9,474,334 B2 | 10/2016 | Jonsson et al. | |
| D772,418 S | 11/2016 | Dunn et al. | |
| 9,492,301 B2 | 11/2016 | Hu et al. | |
| D776,288 S | 1/2017 | Dunn et al. | |
| D776,289 S | 1/2017 | Dunn et al. | |
| 9,668,907 B2 | 6/2017 | Romo et al. | |
| 9,744,065 B2 | 8/2017 | Walborn et al. | |
| 9,839,548 B2 | 12/2017 | Ingvarsson et al. | |
| 9,839,549 B2 | 12/2017 | Walborn et al. | |
| 9,839,550 B2 | 12/2017 | Walborn et al. | |
| 10,667,939 B2 | 6/2020 | Kim | |
| 10,702,413 B2 | 7/2020 | Kim | |
| 2002/0095105 A1 | 7/2002 | Jensen | |
| 2002/0095750 A1 | 7/2002 | Hammerslag | |
| 2002/0128574 A1 | 9/2002 | Darby | |
| 2003/0093882 A1 | 5/2003 | Gorza et al. | |
| 2003/0171703 A1 | 9/2003 | Grim et al. | |
| 2003/0204938 A1 | 11/2003 | Hammerslag | |
| 2004/0010212 A1 | 1/2004 | Kuiper et al. | |
| 2004/0019307 A1 | 1/2004 | Grim et al. | |
| 2004/0167453 A1 | 8/2004 | Peters | |
| 2005/0060914 A1* | 3/2005 | Fuerst | A43B 7/141 |
| | | | 36/102 |
| 2005/0131324 A1 | 6/2005 | Bledsoe | |
| 2005/0145256 A1 | 7/2005 | Howard et al. | |
| 2005/0165338 A1 | 7/2005 | Iglesias et al. | |
| 2005/0171461 A1* | 8/2005 | Pick | A61F 5/0111 |
| | | | 602/27 |
| 2005/0172517 A1 | 8/2005 | Bledsoe et al. | |
| 2005/0187505 A1 | 8/2005 | Carlson | |
| 2005/0274046 A1 | 12/2005 | Schwartz | |
| 2006/0048344 A1 | 3/2006 | Cavanagh et al. | |
| 2006/0084899 A1 | 4/2006 | Verkade et al. | |
| 2006/0135899 A1 | 6/2006 | Jerome et al. | |
| 2006/0135902 A1 | 6/2006 | Ingimundarson et al. | |
| 2006/0156517 A1 | 7/2006 | Hammerslag et al. | |
| 2006/0189907 A1 | 8/2006 | Pick et al. | |
| 2006/0217649 A1 | 9/2006 | Rabe | |
| 2006/0229541 A1 | 10/2006 | Hassler et al. | |
| 2007/0011914 A1* | 1/2007 | Keen | A43B 5/08 |
| | | | 36/50.1 |
| 2007/0055188 A1 | 3/2007 | Avni et al. | |
| 2007/0167884 A1 | 7/2007 | Mangrum et al. | |
| 2007/0169378 A1 | 7/2007 | Sodeberg et al. | |
| 2007/0185425 A1 | 8/2007 | Einarsson et al. | |
| 2007/0191749 A1* | 8/2007 | Barberio | A61F 5/0106 |
| | | | 602/5 |
| 2007/0282230 A1 | 12/2007 | Valderrabano et al. | |
| 2007/0293798 A1* | 12/2007 | Hu | A61F 5/0195 |
| | | | 602/27 |
| 2008/0060167 A1 | 3/2008 | Hammerslag et al. | |
| 2008/0060168 A1 | 3/2008 | Hammerslag et al. | |
| 2008/0066272 A1 | 3/2008 | Hammerslag et al. | |
| 2008/0066345 A1 | 3/2008 | Hammerslag et al. | |
| 2008/0066346 A1 | 3/2008 | Hammerslag et al. | |
| 2008/0083135 A1 | 4/2008 | Hammerslag et al. | |
| 2008/0294082 A1 | 11/2008 | Chang et al. | |
| 2008/0294083 A1 | 11/2008 | Chang et al. | |
| 2008/0319362 A1* | 12/2008 | Joseph | A61F 5/055 |
| | | | 602/7 |
| 2009/0012482 A1 | 1/2009 | Pinto et al. | |
| 2009/0099495 A1 | 4/2009 | Campos et al. | |
| 2009/0227927 A1* | 9/2009 | Frazer | A61F 5/34 |
| | | | 602/27 |
| 2009/0234260 A1 | 9/2009 | Coward et al. | |
| 2009/0270820 A1 | 10/2009 | Johnson et al. | |
| 2009/0287127 A1 | 11/2009 | Hu et al. | |
| 2009/0287128 A1 | 11/2009 | Ingimundarson et al. | |
| 2010/0069808 A1 | 3/2010 | Mitchell | |
| 2010/0100020 A1 | 4/2010 | Fout et al. | |
| 2010/0234782 A1 | 9/2010 | Hu et al. | |
| 2010/0287793 A1* | 11/2010 | Hall | A43B 5/0401 |
| | | | 36/114 |
| 2010/0324461 A1 | 12/2010 | Darby, II et al. | |
| 2011/0009791 A1 | 1/2011 | Hopmann | |
| 2011/0015555 A1 | 1/2011 | Anderson et al. | |
| 2011/0196275 A1 | 8/2011 | Chang et al. | |
| 2012/0010534 A1 | 1/2012 | Kubiak et al. | |
| 2012/0035560 A1 | 2/2012 | Eddy et al. | |
| 2012/0078148 A1 | 3/2012 | Hu et al. | |
| 2012/0130292 A1* | 5/2012 | Benjoar | A43B 7/146 |
| | | | 601/136 |
| 2012/0220960 A1 | 8/2012 | Ruland | |
| 2012/0238924 A1 | 9/2012 | Avni | |
| 2013/0018294 A1 | 1/2013 | Jones et al. | |
| 2013/0066247 A1 | 3/2013 | Bird et al. | |
| 2013/0310721 A1 | 11/2013 | Hu et al. | |
| 2014/0039368 A1* | 2/2014 | Perkins | A61F 5/0111 |
| | | | 602/12 |
| 2014/0128789 A1 | 5/2014 | Chen | |
| 2014/0171837 A1 | 6/2014 | Harcourt | |
| 2014/0265018 A1 | 9/2014 | Grim et al. | |
| 2014/0276310 A1 | 9/2014 | Grim et al. | |
| 2014/0350446 A1 | 11/2014 | Gunnsteinsson | |
| 2015/0075030 A1 | 3/2015 | Walborn et al. | |
| 2015/0088046 A1 | 3/2015 | Walborn et al. | |
| 2015/0164179 A1 | 6/2015 | Walborn et al. | |
| 2016/0000174 A1* | 1/2016 | Grim | A61F 5/0111 |
| | | | 36/97 |
| 2016/0213823 A1 | 7/2016 | Walborn et al. | |
| 2017/0216078 A1* | 8/2017 | Rivlin | A61F 5/05866 |
| 2017/0296373 A1* | 10/2017 | Bean | A61F 5/0127 |
| 2019/0076286 A1 | 3/2019 | Kim | |
| 2019/0142622 A1 | 5/2019 | Kim | |
| 2019/0240057 A1 | 8/2019 | Gunnsteinsson et al. | |

FOREIGN PATENT DOCUMENTS

| | | | |
|---|---|---|---|
| EP | 2147664 A1 | 1/2010 | |
| EP | 2468323 A1 | 6/2012 | |
| EP | 3431056 A1 | 1/2019 | |
| FR | 2 399 811 A1 | 3/1979 | |
| FR | 2634988 A1 | 2/1990 | |
| FR | 2 681 516 A1 | 3/1993 | |
| GB | 2 124 473 A | 2/1984 | |
| GB | 2 178 940 A | 2/1987 | |
| JP | 2005211626 A | 8/2005 | |
| KR | 101243558 B1 | 3/2013 | |
| KR | 20150019768 A | 2/2015 | |
| KR | 101694792 B1 | 1/2017 | |
| KR | 101694805 B1 | 1/2017 | |
| WO | 93/13685 A1 | 7/1993 | |
| WO | 93/24081 A1 | 12/1993 | |
| WO | 94/18863 A1 | 9/1994 | |
| WO | 97/36507 A1 | 10/1997 | |
| WO | 2004/021817 A1 | 3/2004 | |
| WO | 2006035469 A2 | 4/2006 | |
| WO | 2006045079 A1 | 4/2006 | |
| WO | 2007078845 A2 | 7/2007 | |
| WO | 2010104824 A1 | 9/2010 | |
| WO | 2013/084213 A1 | 6/2013 | |
| WO | 2014032029 A1 | 2/2014 | |
| WO | 2015006766 A1 | 1/2015 | |
| WO | WO-2017160064 A1 * | 9/2017 | A41D 13/0543 |

OTHER PUBLICATIONS

FoamSealant, What is an EVA foam and its common uses, May 25, 2015, https://foamsealant.com.au/what-is-an-eva-foam-and-its-common-uses/ (Year: 2015).*

Product Information Sheet: XP Walker (extra pneumatic), Aircast, Jan. 1, 2008, 4 pages. Retrieved from the internet, http://www.aircast.com/index.asp/fuseaction/products.detail/cat/2/id/76.

(56) References Cited

OTHER PUBLICATIONS

Product Information Sheet: Nextep Contour Walker, Procare, DJ Orthopedics, Jan. 1, 2008, 1 page. Retrieved from the internet, www.djortho.com.
Product Information Sheet: Nextep Contour w/Air Walker, Procare, DJ Orthopedics, Jan. 1, 2008, 1 page. Retrieved from internet, www.djortho.com.
Product Information Sheet: XP Achilles Walker (EU only), Aircast, Jan. 1, 2008, 4 pages. Retrieved from the internet, http://www.aircast.com/index.asp/fuseaction/products.detail/cat/2/id/104.
Product Information Sheet: XP Diabetic Walker System, Aircast, Jan. 1, 2008, 4 pages. Retrieved from the internet, http://www.aircast.com/index.asp/fuseaction/products.detail/cat/2/id/15.
Product Information Sheet: SP Walker (short pneumatic), Aircast, Jan. 1, 2008, 4 pages. Retrieved from the internet, http://www.aircast.com/index.asp/fuseaction/products.detail/cat/2/id/14.
Product Information Sheet: FP Walker (foam pneumatic), Aircast, Jan. 1, 2008, 4 pages. Retrieved from the internet, http://www.aircast.com/index.asp/fuseaction/products.detail/cat/2/id/75.
"Eva Explained, What Is It?," Monmouth Rubber & Plastics, 2019, 4 Pages.
Hanhi et al., "Elastomeric Materials," Tampere University of Technology, The Laboratory of Plastics and Elastomer Technology, 2007, 84 Pages.

"Aircast AirSelect Standard Patient Information," DJO Global, 2013, 1 Page.
"FP Walker Foam Pneumatic," Aircast, 2 Pages, Downloaded on Feb. 4, 2019.
"Airselect Standard," DJO, Downloaded from https://www.djoglobal.com/products/aircast/airselect-standard, 2019, 4 Pages.
"Genesis Walker The lightest Full Shell Walker Boot on the Market," Breg Inc, 2015, 6 Pages.
"FP Walker (Foam Pneumatic)," DJO, Downloaded from https://www.djoglobal.com/products/aircast/fp-walker-foam-pneumatic, 2019, 4 Pages.
"Rebound Air Walker the Standard in Foot and Ankle Care," Ossur, Mar. 2016, 4 Pages.
"Townsend XLR8 Pneumatic Walker," Townsend AThuasne Company, downloaded from www.townsenddesign.com on Feb. 4, 2019, 4 Pages.
International Search Report from PCT Application No. PCT/US2019/016462, May 17, 2019.
Office Action from corresponding Chinese Application No. 201980011136.3, Jul. 21, 2022.
Office Action from corresponding Chinese Application No. 201980011136.3, Dec. 2, 2021.
International Search Report and Written Opinion from PCT Application No. PCT/US2021/059657, Apr. 7, 2022.
Partial International Search Report from PCT Application No. PCT/US2021/059657, Feb. 16, 2022.

* cited by examiner

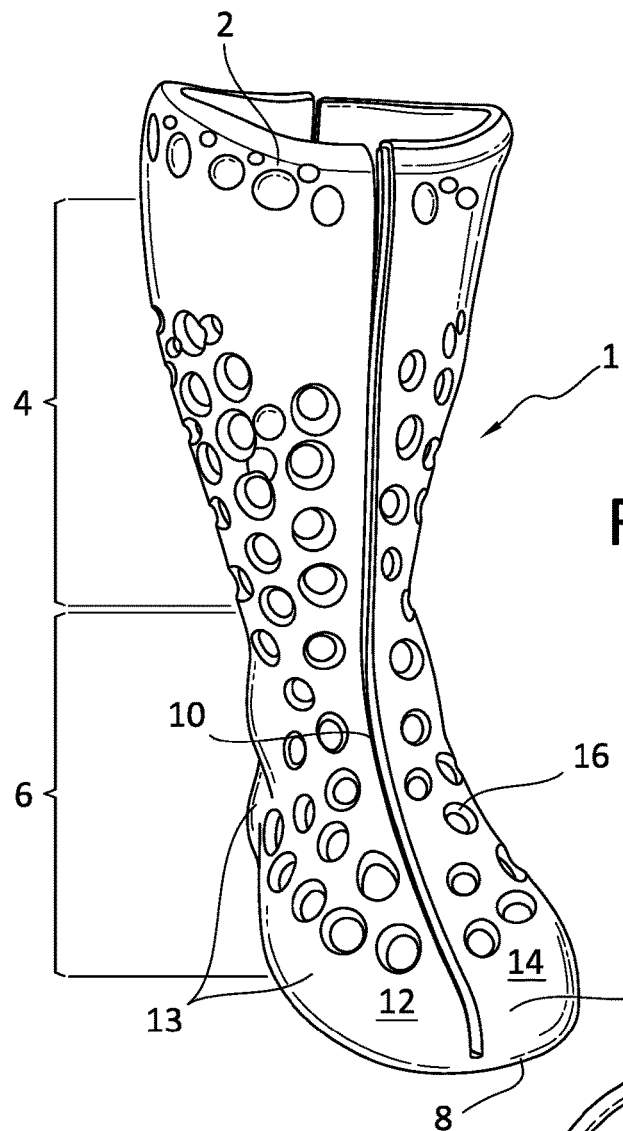
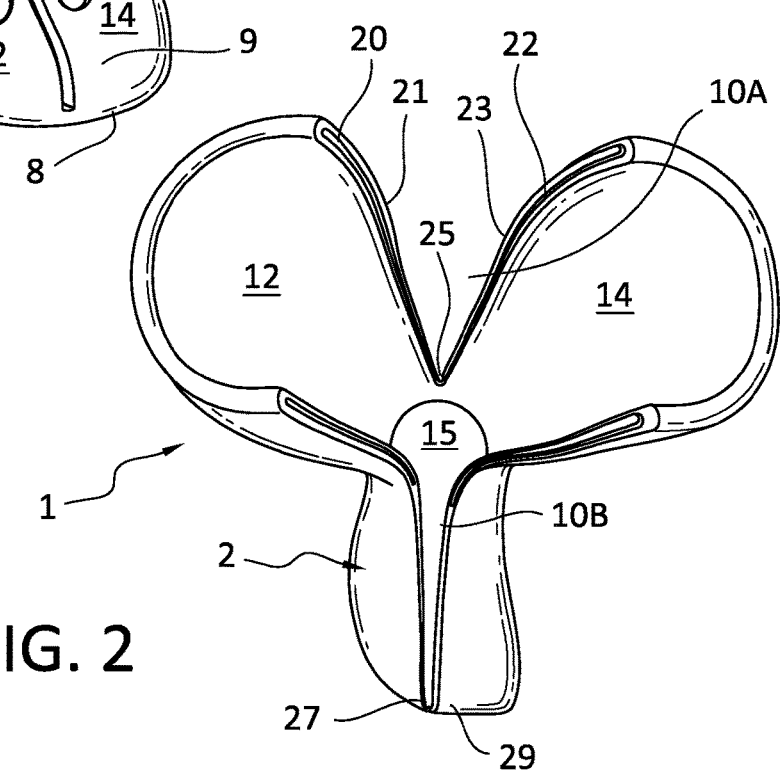
FIG. 1
FIG. 2

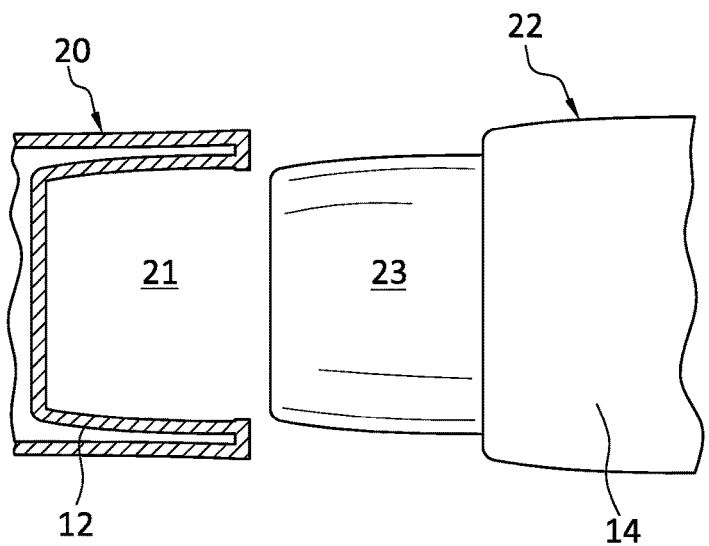
FIG. 3
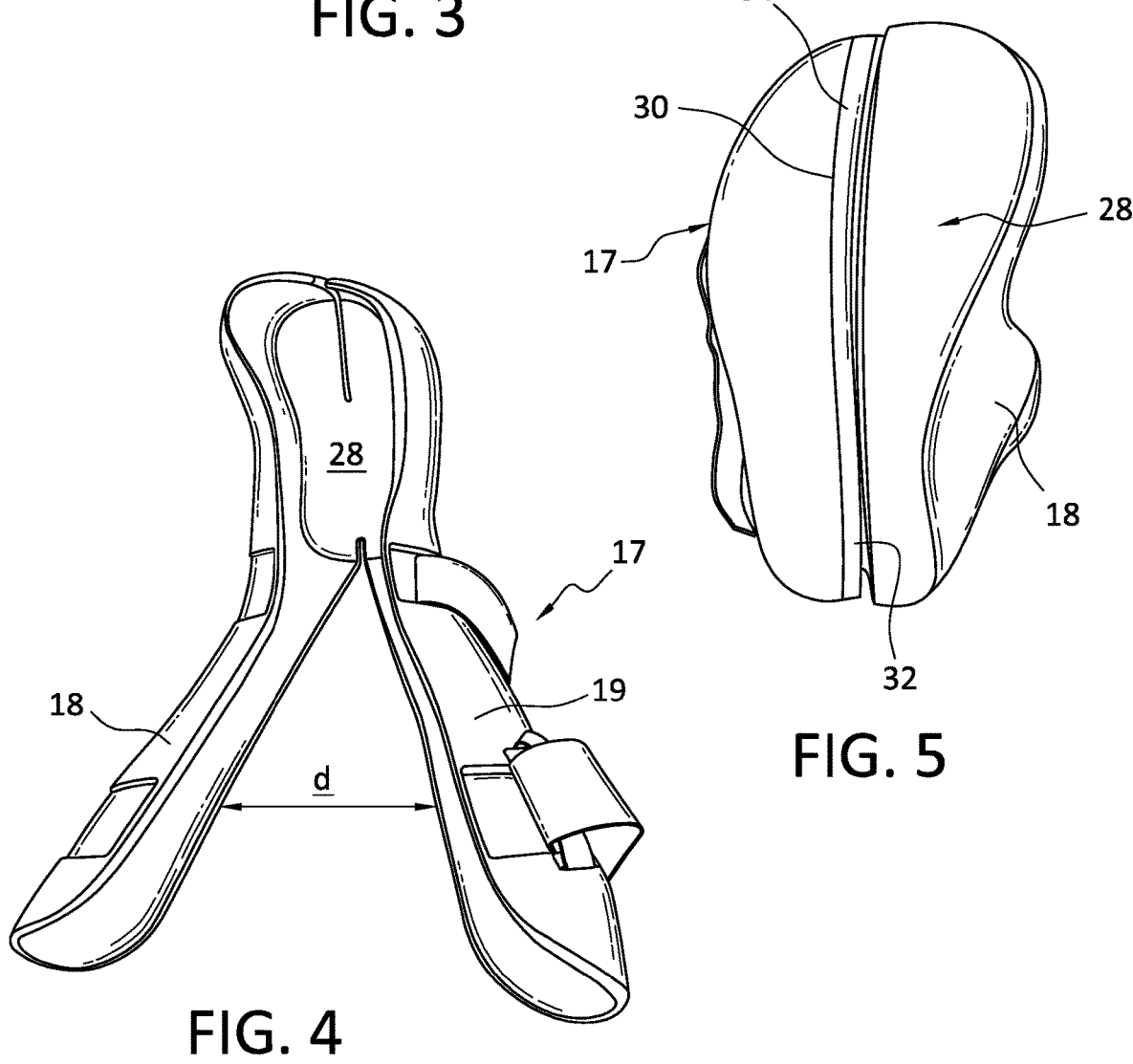
FIG. 4
FIG. 5

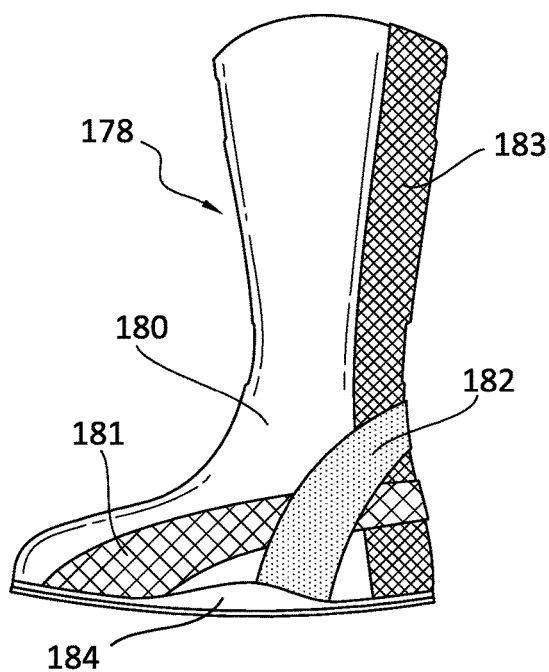
FIG. 10D
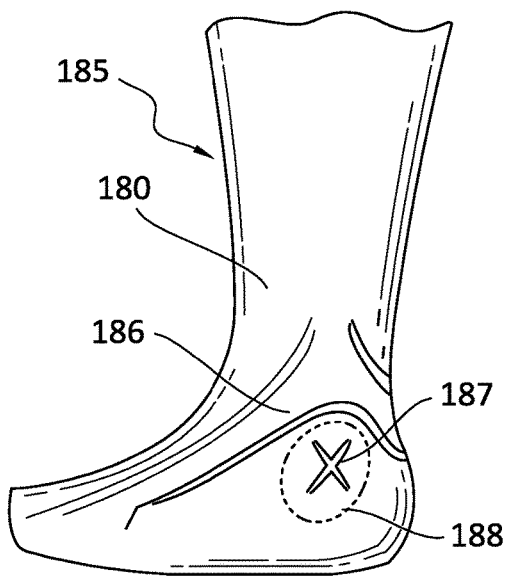
FIG. 10E
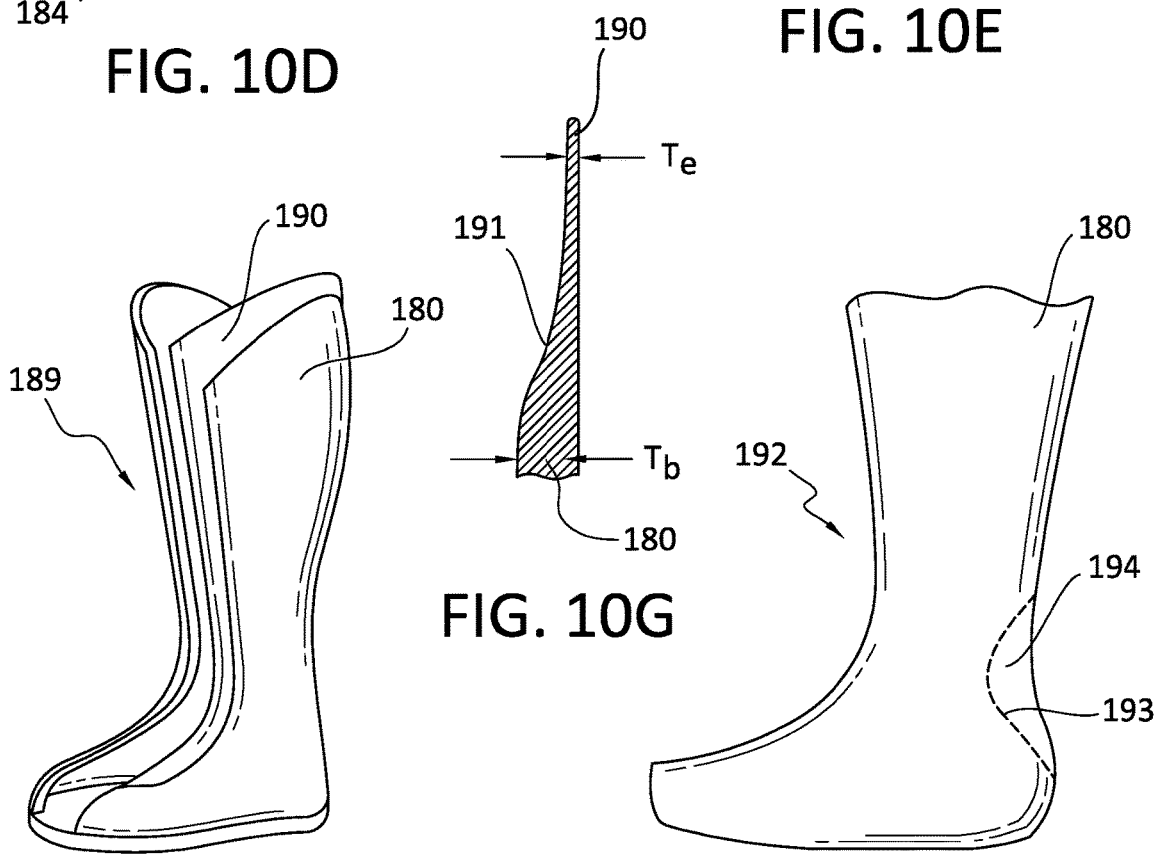
FIG. 10F
FIG. 10G
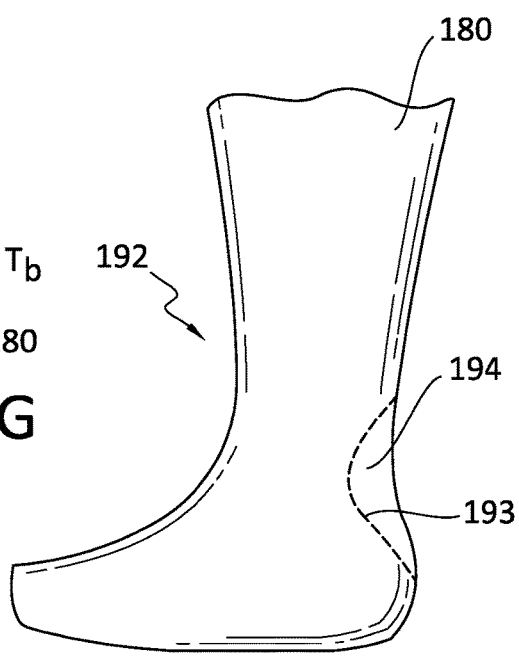
FIG. 10H

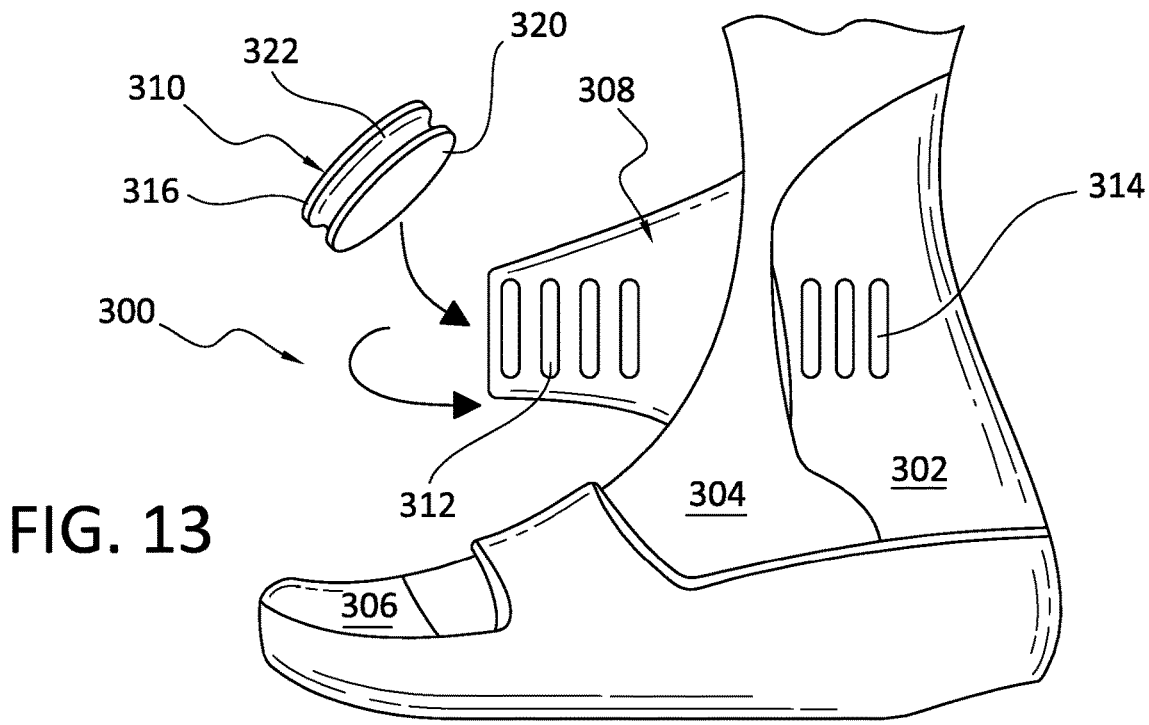
FIG. 13
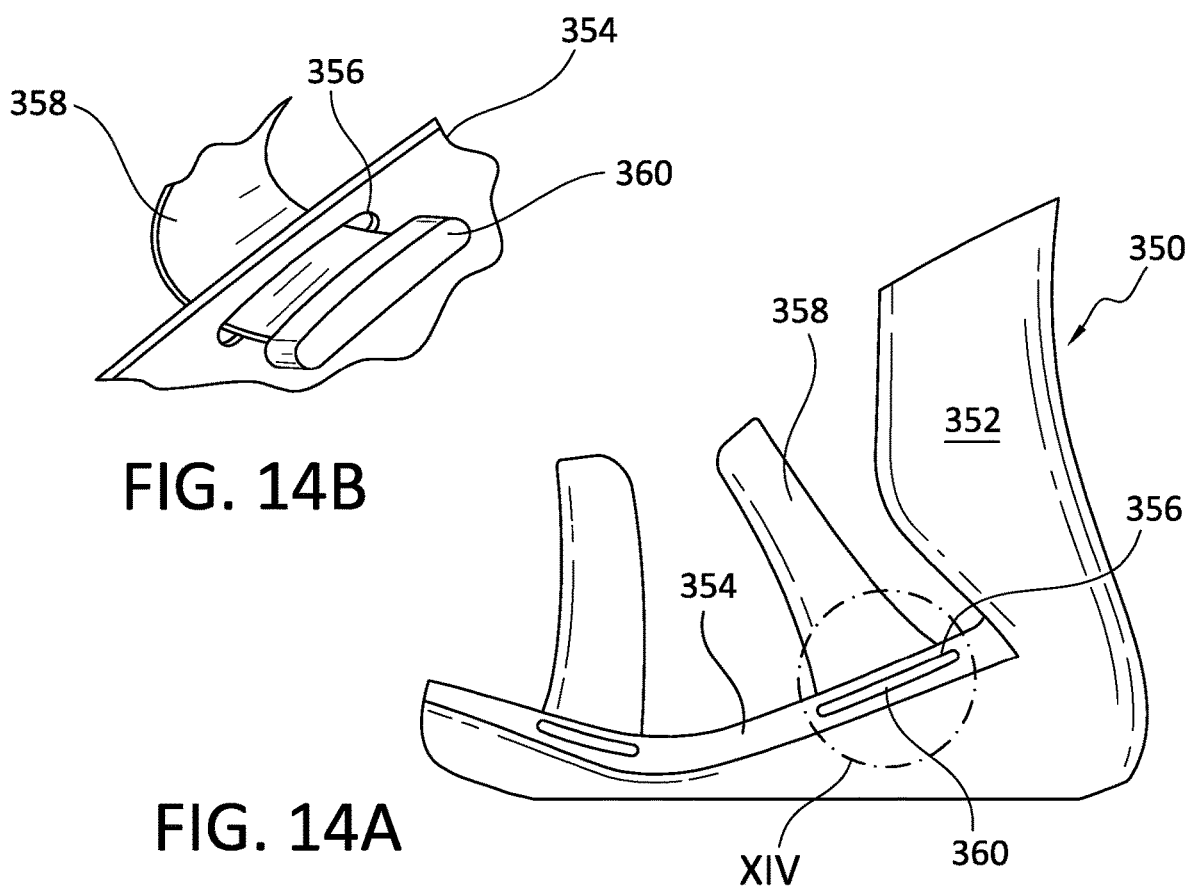
FIG. 14B
FIG. 14A

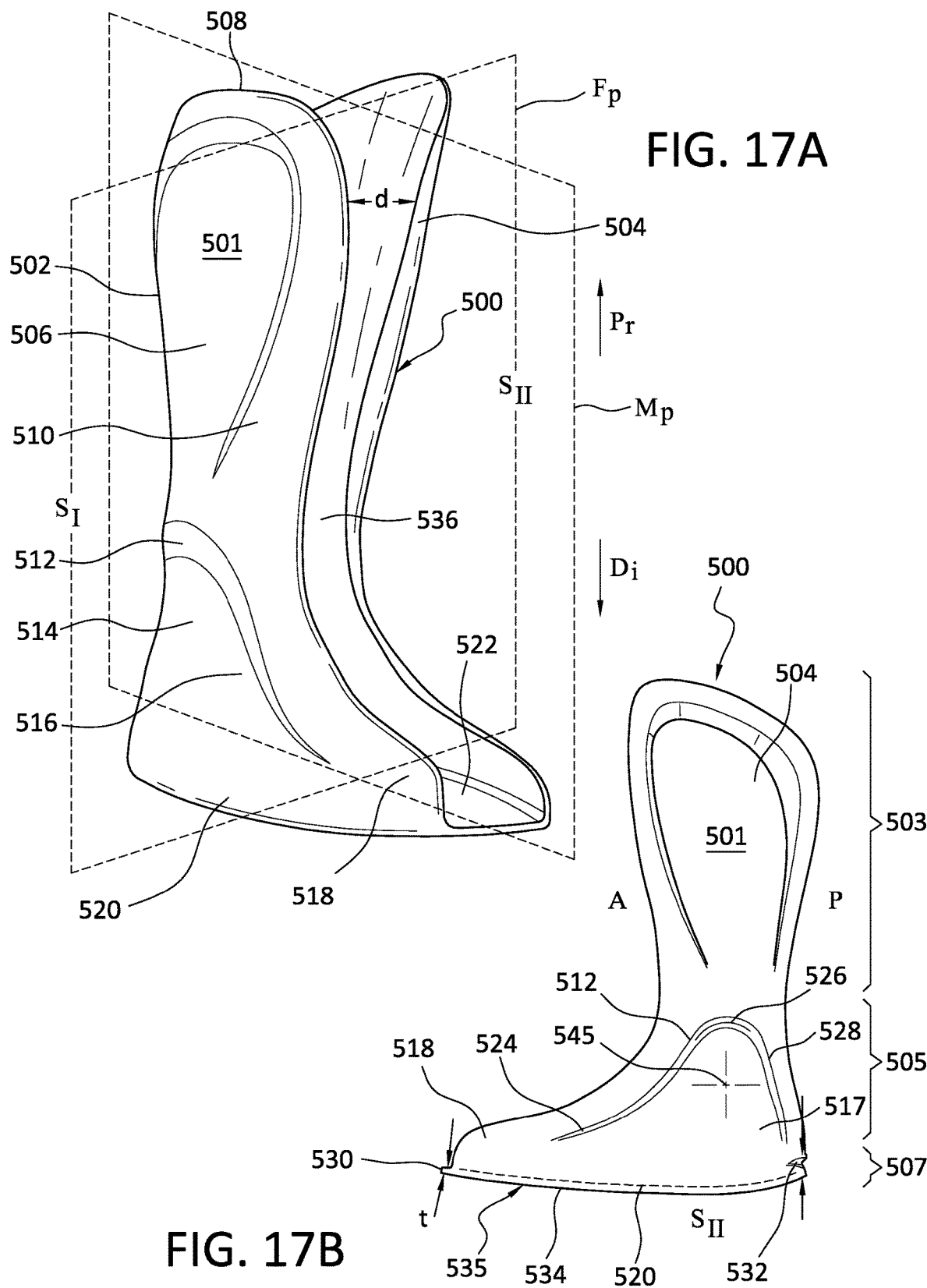

ORTHOPEDIC WALKER

BACKGROUND

Sprains, fractures, and soft tissue injuries involving the lower leg and foot commonly result from household accidents, workplace incidents, and sports related trauma. Other wounds or sensitive areas in the lower limbs may result from surgical intervention or the effect of certain medical conditions. These injuries affect a broad range of individuals and, while not life threatening, can increase in severity without treatment, stabilization, and/or protection.

Prior art solutions for treating, stabilizing, and/or protecting the lower limb after injury or surgery can be categorized into two approaches: casting systems and orthopedic braces. Each approach can provide the required rigid support to a user's limb, with distinct disadvantages and drawbacks.

Known casting systems are typically fabricated directly on the limb of a user and can conform directly to the unique anatomy of a user. The casting systems comprise an interior padding and an exterior layer of materials moldable in a first state before transitioning into a rigid material state, e.g. molded plasters or resins applied to a limb and then hardened in place. The casting systems are often difficult and messy to create, are not adjustable once hardened, are not easily removed without being destroyed, are not reusable, are not breathable or hygienic, and must be worn for long, uninterrupted periods.

Orthopedic braces include a wide range of splints, braces, and walking boots. The braces can be mass-produced and are formed of complex multicomponent systems that allow adjustment or tightening to the limb of a user. Such multicomponent systems often include several straps or other securing means, with rigid plastic shells or splints for securing a padded structure around a limb, enclosing or wrapping the limb in both a soft or padded internal covering, with a harder frame or external shell. The complexity of the multicomponent systems and the cost of the required materials render orthopedic braces uneconomical for personalized construction conforming to the anatomy or treatment needs of a user.

There is a need for a stabilizing solution that is adaptable to the anatomy of a user at a low cost, and that is adjustable about the limb of a user, with fewer or no complex multicomponent systems.

Further, both the unadaptable casting systems and the complex orthopedic braces are bulky and heavy. The exterior surface of a cast may be rough, while the surface profile of an orthopedic brace is uneven, and each can frequently disrupt the use of clothing, furniture, and/or bedding, or cause uncomfortable contact against another limb of the user. There is a further need for a solution that not only is more comfortable around the limb, but also that is lighter and streamlined in construction and more convenient in use.

An additional challenge in existing devices, including conventional strut walkers, is the unyielding, uncomfortable, and inconvenient nature of existing immobilization techniques. Conventional strut walkers, for example, comprise a foot plate and two unyielding struts (frequently metal) that are arranged with a shell to provide immobilization of a portion of a user's anatomy. The unyielding characteristics of conventional devices, provided for immobilization, yield a device that is difficult to adapt to a user's individual needs and dimensions, especially around the lower leg, particularly because existing devices are often provided based on a user's shoe size but not based on the size of their lower leg. There is accordingly a need for a device that provides needed immobilization while minimizing the challenges presented by the unyielding nature of existing devices.

The orthopedic walker or walking boot of the disclosure bridges the gap between the two prior art solutions, providing the advantages of a solution adjustably conforming to the individual anatomy of a user, and without the related drawbacks of added weight, complexity, and cost.

SUMMARY

An orthopedic walker or walking boot is arranged with a construction for facilitating donning and doffing and which provides a limb with reliable protection and support is described.

The walker may be configured as having a semi-rigid body material to reduce the complexity, cost, and weight of the walker. The semi-rigid nature of the body material provides rigid support to the limb and allows the walker to resiliently hold or return to its original shape, while having flexibility or resiliency to facilitate regular and comfortable donning and doffing. While a semi-rigid body material is preferable, other types of materials are envisioned.

The walker combines the strength, support, and customized fit of a casting system with the adjustability and other functional and structural advantages of an orthopedic brace. Due to the use of a semi-rigid body material, the walker may be advantageously manufactured with a unitary form construction or of a single-part construction or of multiple components. The semi-rigid body material may preferably constitute a unitary construction to provide a comfortable and readily adjustable fit about a limb with no additional splints, supports, padding, or other components as required in prior art devices. The semi-rigid body material further reduces the cost and weight of the walker relative to casting systems and conventional orthopedic braces.

Material properties of a body of the walker can be adjusted to accommodate the desired fit and hold of the walker. Increased elasticity can urge the walker body towards a closed position over a limb, helping to secure the walker on the limb of a user during periods of activity. Increased rigidity can be used for injuries where protection from external forces is most important and/or provided in regions requiring greater immobilization or support.

The walker body can be advantageously configured with a smooth, streamlined, and soft surface both on an interior and exterior surface of the walker, while retaining enough strength to stabilize the limb. The smooth surface prevents the walker from catching on clothing or other objects such as knee scooters or crutches, or from causing discomfort during sleep or other activities.

The material used in the walker body may be selected based on the needs of individual users and/or activity levels. A thicker or higher density material may be used for more active users, while a thinner or lower density material may be used for less active users. The variation of material properties of the walker body may be adjusted based on the injury of a user and the user's activity level and can treat many injuries and users.

In a similar way, embodiments described may herein use varying material properties, including different thicknesses, densities, or hardnesses of body material, to adjust the flexibility and resiliency of different portions of the walker about a limb. Injured areas may receive greater support, compression, immobilization, or protection while other areas are provided with increased mobility and comfort.

In an embodiment, the thickness and/or density of the body material of the walker body may increase from a proximal end to a distal end of the walker body, providing increased support to an injured foot or ankle region while retaining a comfortable fit about a lower leg region particularly for users having differently sized legs.

In another embodiment, the thickness and/or density of the body material of the walker body may be greater at medial and/or lateral portions, or at anterior and/or posterior portions, to form a support having properties like the effect of a splint or frame but without the added complexity, cost, or weight. The increased thickness and/or density can create increased support against medial and lateral rotation and/or against anterior and posterior rotation. A walker body may be customized to treat an injury, such as a sprain, or to accommodate the needs of a user without adding complex splints, padding, or other components.

An exemplary body material may be an expanded plastic. By understanding expanded plastic, it is understood that the plastic may be porous or foam-like, such as closed-cell. The expanded plastic may be selected due to its stiffness, either in the material composition or structurally, such as by thickness, or according to both. An example of an expanded plastic is ethylene-vinyl acetate (EVA), which may be an expanded rubber or foam rubber, and is an elastomeric polymer that produces materials having rubber-like softness and flexibility. The EVA may have different proportions of vinyl-acetate which structurally may modify the toughness and stiffness of the EVA. Other polymeric materials may form the body and may be selected from the non-limiting group comprising polyurethane, polyethylene, and polypropylene.

The expanded plastic offers a stiff but lighter body than in conventional orthopedic walkers. The expanded plastic also allows for flexibility that facilitates donning of the walker. Donning and doffing of the unitary form walker may be facilitated by at least one opening provided in the walker body, which may be in the form of an elongate opening or another form. The at least one opening may be configured to partially divide the walker body into a first side and a second side along a limb-receiving region of the walker. The at least one opening may extend along the length of the limb-receiving region to allow a user to fold back the first and second sides of the walker to insert a limb into the limb-receiving region without excessive bending of an injured limb or joint. This may advantageously provide for easier donning from a supine position, e.g. post-surgery.

The at least one opening may also be configured to allow access to the limb while the walker body is secured to a limb. The walker body may secure an ankle of a user, while also having an elongate opening exposing a proximal side of a foot and toes. Such a configuration allows a clinician to access bandaging about the foot, allows additional space for injured toes, and/or provides increased ventilation of the proximal side of the foot without sacrificing needed stability, immobilization, or support.

In embodiments where the at least one opening may only extend along the limb-receiving region of the walker, a bottom surface of the walker may retain increased structural integrity and provide increased protection and comfort for a user.

The at least one opening may be arranged such that the first side and the second side of the walker body are configured as lateral and medial portions, or as anterior and posterior portions. In a variation, the at least one opening may extend in a longitudinal and a transverse direction such that the at least one opening wraps or spirals around the limb receiving region of the orthopedic walker.

In another embodiment, the at least one opening in the walker body may define at least two elongate openings, which partially divide the body of the walker into the first side and the second side along the limb receiving region of the walker. The at least two elongate openings can be arranged such that the first side and the second side are configured as lateral and medial portions, or as anterior and posterior portions. In a variation, one or both of the at least two elongate openings can extend in both the longitudinal and transverse direction.

The bottom surface of the walker body may be provided with a recessed portion to facilitate donning and doffing of the walker. The recessed portion may be configured to allow the first side and the second side of the walker body to expand apart, providing a larger opening for insertion or removal of the limb of the user.

In one example, the recessed portion may be configured to extend from a posterior end to an anterior end of the bottom surface, and to provide a joint or vertex for the separation of lateral and medial sides of the walker. In this way the walker body may be advantageously opened and applied to the limb of the user without requiring the user to move or manipulate the limb, such as when the user is lying supinely in a hospital bed.

Variations in placement and configuration of the recessed portion and the at least one opening are possible, as understood by one of ordinary skill in the art from the detailed description of the exemplary embodiments.

According to an embodiment, the at least one opening of the walker body is defined by a first edge of the walker body opposite a second edge. The first edge has a receiving recess along at least a portion of its length and the second edge has a protruding part along at least a portion of its length corresponding to the receiving recess of the first edge. The receiving recess is arranged to receive the protruding part and facilitate the closure of the at least one opening of the walker body, improving the fit and closure of the walker about the limb of a user. One or both of the receiving recess and the protruding part may be arranged with friction-enhancing elements to improve the connection between the first and second edges.

The combination of the protruding part and the receiving recess enables the walker body to better resist external forces by locking the first and second sides of the walker body together. Further, the combination of the protruding part and the receiving recess advantageously avoids overlap in the edges of the walker body, which in prior art devices causes uneven closure and sliding at the overlapping edges, reducing comfort and compliant and/or effective use.

The protruding part and the receiving recess may be configured with complementary shapes or surfaces for improving a locking of the first and second sides of the walker body. In an exemplary embodiment the protruding part may have a J-hook or other suitable shape arranged to engage a corresponding notch or shape within the receiving recess. In a variation, the protruding part and the receiving recess may be provided with a friction-enhancing surface texture.

In another variation, the first edge and the second edge may each include at least one receiving recess and at least one protruding part. The at least one receiving recess and the at least one protruding part of each of the first and second edges may be arranged with corresponding shapes to create a zipper-like fastening of the first and second sides of the walker body.

As described, the locking or coupling of the first edge and the second edge or of the at least one protruding part and the at least one receiving recess to each other may be affected through the resiliency of the walker body, and/or a force exerted by a user, to bring the first edge and the second edge together in alignment. A closing means may also be provided to secure the walker about the limb of the user.

The walker body may further be provided with at least one securing element to secure and/or tighten the walker body about the limb of the user. The at least one securing element may include a hook and loop fastener, straps, buckles, or other means of closing or securing provided on the walker body, wrapped around the walker, etc.

The walker body may be advantageously configured with at least one receiving element for receiving the at least one securing element with no additional components. The at least one receiving element may comprise at least one channel, hole, slot, slit, or opening in the walker body.

If the at least one receiving element is configured as at least one channel, hole, slot, slit or opening, the at least one receiving element may extend a distance into and/or through the semi-rigid material of the walker body into the limb-receiving region of the walker body.

The at least one securing element can be threaded through the at least one receiving element, such that the at least one securing element is integrated into the walker body and provides a tight fit against the limb of the user. The walker body may be provided with channels in or holes through an exterior surface of the walker body at locations corresponding to the anatomical shape of the limb, such as at a calf, for securing to users of different anatomical sizes/shapes. In some configurations, the at least one receiving element may include a receiving element in the bottom surface of the walker body. Such a configuration can be advantageous in securing the walker to the foot of a user.

In view of the foregoing description, and the embodiments disclosed herein, this disclosure enables one of ordinary skill in the art to arrange the at least one securing element and the at least one receiving element according to the anatomy and/or needs of the user.

The walker body may be provided with a plurality of openings arranged to provide ventilation between the exterior and interior of the walker. In a variation, the walker body may be provided with channels for conducting moisture away from a limb and towards the plurality of openings. This arrangement makes it possible to increase ventilation for cooling and drying a limb within the walker body over prior art devices and methods.

The walker body may be made in different sizes and/or may be modifiable to fit a user or limb. In an embodiment, the walker body may be provided with cutting indicia for adjusting the length or size of the walker. Cutting indicia may also be provided along other portions of the walker for selectively removing one or more portions of the walker body to reduce weight of the walker body, relieve pressure points over an affected area, or to facilitate medical treatment of a particular area. In an embodiment, the at least one protruding part may be configured to have an excess length, such that the at least one protruding part may be trimmed to adjust the size of the limb receiving portion of the walker body.

From the foregoing, a simple modification of the walker body and an adaptation to a short limb or a swollen limb is possible. The expense of cutting off segments of the walker body is minimal relative to the components of adjustable frames of prior art devices, and the requirement to rearrange the parts with each use is eliminated. The unitary walker eliminates the additional weight and complexity of multi-component systems. The bottom surface of the walker may be configured as a sole, and arranged with a rocker-type shape, a friction enhancing surface pattern, and/or with a variable thickness or rigidity to allow a user to more comfortably ambulate.

In a variation, a separate outsole, or similarly a slipper sole, can be attached to the bottom surface of the walker body for providing additional support. The outsole may secure to the walker body through any suitable means, and can provide increased protection and support including a rocker-type shape, a friction enhancing surface pattern, and/or variable thickness or rigidity to allow a user to more comfortably ambulate, etc. In an embodiment, the outsole may be configured to have a configuration allowing for an improved connection to the walker body. The exterior surface of the walker body may be provided with at least one receiving recess corresponding to at least one protruding part in the outsole.

In such a configuration, after the user has donned the walker, the outsole may be easily and simply secured to the walker body without significant effort or expense. Similarly, the outsole may be removed for a subsequent doffing or adjustment of the walker about the limb of the user. In the embodiments having a receiving recess and a protruding part described above, the receiving recess and the protruding part may be positioned to avoid sensitive or injured areas of a limb, and/or to provide an improved attachment.

In some embodiments, a shield portion may be attached to the walker body for providing increased protection to certain portions of the limb of the user. The shield portion may comprise the same or similar material as the walker body and may similarly include at least one receiving element for receiving the at least one securing element of the walker body. In an exemplary embodiment, a shield portion may comprise a covering for an open-toe walker body. Such a configuration provides the advantages of an open-toe walker body with the added protection of a closed toe configuration.

An interior surface of the walker body may be provided with a friction-enhancing surface texture, or with a plurality of protrusions, along an entirety of the interior of the walker or at certain locations requiring greater friction or cushioning. By providing the friction-enhancing surface or the plurality of protrusions, a stronger and more resilient fit between the limb and the walker may be established. The surface texture or the plurality of protrusions may be configured with a variable extension length, to increase the comfort or fit for a user, or to cushion a pressure point. The interior surface of the walker may be provided with a padding for increasing user comfort. Memory foam or similar material may be secured to a malleolus portion of the walker to soften contact with the walker body and to provide improved engagement between the walker body and limbs of users of different dimensions.

The limb-receiving region itself has both an upper receiving section and a lower receiving section. The upper receiving section having either a cylindrical or a conical basic form, e.g. a tubular basic form, such that the upper receiving section conforms to the shape of a limb. The lower receiving area may have a shape conforming to a foot or other limb and may be provided with an open or a closed toe.

The semi-rigid body material may comprise EVA, a rubber foam, a closed cell foam, a foam-like material, or any other suitable material having the requisite material properties described previously. Materials are preferred that reduce the weight of the walker body, provide enough strength and support to the limb, and provide enough flexibility to facilitate easy and regular donning and doffing. The semi-rigid body material may have further advantageous properties, e.g. increased durability and comfort. A more durable material lasts longer and is easier to clean. A material that is resistant to solvents and high temperatures, as is the case with EVA, is advantageous as it may be easily cleaned with solvents and/or autoclaved. All these features improve the user's experience while reducing complexity, cost, and bulk.

Embodiments of an orthopedic walker according to the disclosure may be manufactured in many sizes and configurations. Some embodiments may advantageously be configured to be stackable, to be easier to store and ship. In one example, the walker body may be configured to open into a flat state, and a second walker body, a third walker body, and son on may be inserted thereon for stacking and storing the walker bodies.

In another exemplary embodiment, the orthopedic walker has a body formed from at least one polymeric material, and the body defines an upper receiving section, a lower receiving section, and a footbed. The upper receiving section includes first and second portions divided by a median plane of the orthopedic walker. The first and second portions are arranged to individually articulate about or from the median plane to expand or retract a variable distance between the first and second portions of the upper receiving section along one of anterior or posterior sides of the body. As with this embodiment and foregoing embodiments, the embodiment provides the advantage that the walker can be donned on a user when the user is in a supine position, with the first and second portions securing to the leg without the necessity of lifting the leg or knee, which may have recently undergone operation.

The walker body may define at least one opening that separates the first and second portions. The at least one opening is may be at least one elongate opening spacing the first and second portions apart from one another. The at least one opening can taper in width from a proximal end to a distal end of the upper limb receiving portion. The at least one opening may widen from the proximal end to the distal end of the lower limb-receiving portion. The first opening of the at least opening may extend along an entirety of the body on the anterior side of the body from the upper receiving section to the lower receiving section.

According to a variation, the walker body may form at least two openings. The at least two openings may partially separate the upper receiving section of the body into the first and second portions. The at least two openings may be opposite one another generally along the median plane.

The walker body may consist of the upper receiving section, the lower receiving section, and the footbed, and may be formed as a continuous and unitary structure formed from the at least one polymeric material. The at least one polymeric material may be an expanded thermoplastic.

The first and second portions of the upper receiving section may have generally a same or symmetric profile such that the upper receiving section is arranged for both right and left legs of a user. Each of the first and second portions may have a curvilinear profile extending between and among proximal and distal portions of the upper receiving section. The first and second portions may have a convex profile along an inner surface thereof generally corresponding to the concavity of the inner surface. The upper receiving section may have a varying wall thickness.

The lower receiving section can include first and second portions defined by the median plane. The first and second sides of the walker body may have a generally same profile such that the lower receiving section is arranged for both right and left feet of a user. The footbed includes at least one elongate groove extending along or generally parallel to the median plane of the orthopedic walker. The at least one elongate groove may extend along either an inner surface or an outer surface of the footbed and extending a thickness into the footbed.

The body may be arranged to exhibit an increasing rigidity from a proximal end to a distal end. The body can define a curvilinear reinforcement feature generally dividing the upper receiving section from the lower receiving section. The reinforcement feature defines greater rigidity of the body than areas of the body adjacent thereto.

These and other features, aspects, and advantages of the present disclosure will become better understood regarding the following description, appended claims, and accompanying drawings.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of an orthopedic walker, and in no way limit the structures or configurations according to the present disclosure.

FIG. 1 is a perspective view of an embodiment of an orthopedic walker in a closed configuration.

FIG. 2 is a perspective view of the orthopedic walker of FIG. 1 in an open configuration.

FIG. 3 is a schematic view of connecting edges in the orthopedic walker of FIG. 1.

FIG. 4 is a schematic view of another embodiment of an orthopedic walker in an open state.

FIG. 5 is a perspective view of a bottom surface of the orthopedic walker in FIG. 4.

FIG. 10D is a side elevational view of another embodiment of an orthopedic walker.

FIG. 10E is a side elevational view of another embodiment of an orthopedic walker.

FIG. 10F is a perspective view of another embodiment of an orthopedic walker.

FIG. 10G is a detail view taken from FIG. 10F.

FIG. 10H is a side elevational view of another embodiment of an orthopedic walker.

FIG. 13 is a side elevational view of another embodiment of an orthopedic walker.

FIG. 14A is a side elevational view of another embodiment of an orthopedic walker.

FIG. 14B is a detail view taken from detail XIV in the orthopedic walker of FIG. 14A.

FIG. 17A is a perspective view of an orthopedic walker arranged for universal use.

FIG. 17B is a side elevational view of the orthopedic walker of FIG. 17A.

DETAILED DESCRIPTION OF VARIOUS EMBODIMENTS

Figure 6A:
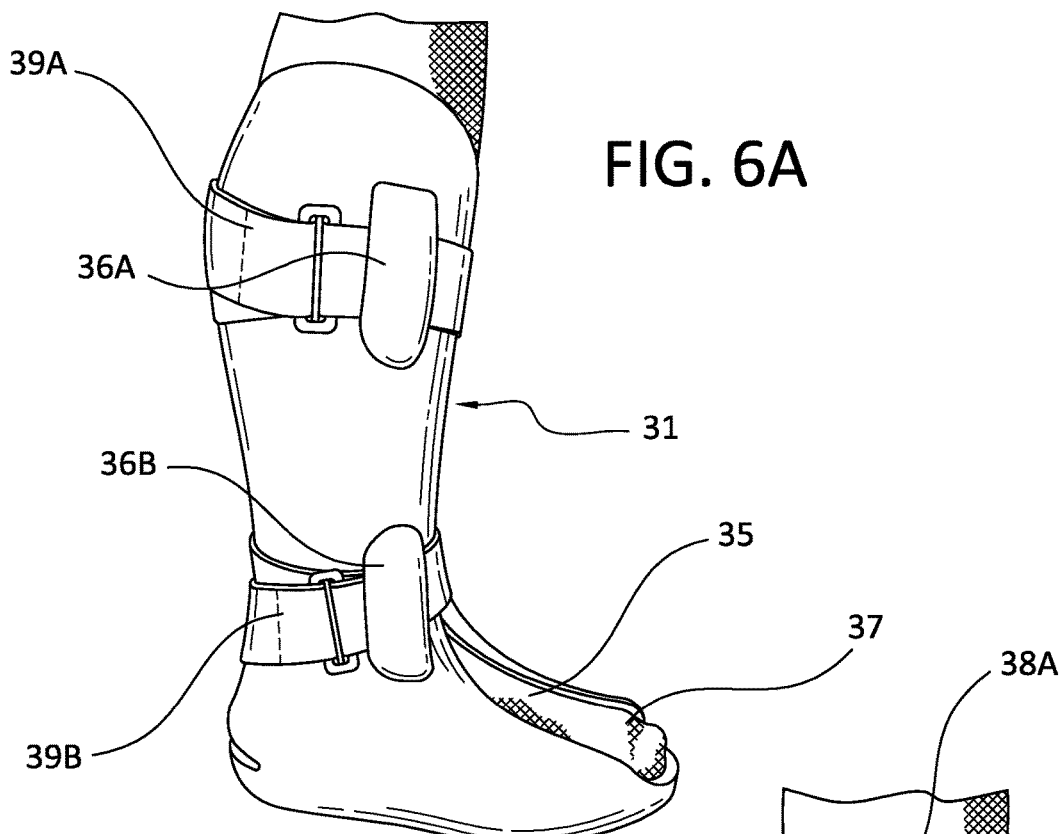
FIG. 6A is a side elevational view of another embodiment of an orthopedic walker.

A. Introduction of Embodiments and Definitions of Terms

Embodiments of an orthopedic walker are used for donning and doffing on a user and are provided for stabilizing and supporting anatomical portions of a user, for example, the lower leg, ankle, and foot of a user.

The walker has a semi-rigid or rigid body material to reduce the complexity, cost, and weight of the walker. The semi-rigid nature of the body material provides rigid support when worn on the limb and allows the walker to resiliently hold or return to its original shape, while having some degree of flexibility or resiliency to facilitate regular donning and doffing. Unlike conventional orthopedic walkers, a preferred embodiment of the walker body is constructed from a single material and obviates the necessity of providing different structural materials. The walker eliminates the need for securing different materials together with adhesives and fasteners and has enough strength and resiliency to withstand normal ground reaction forces incurred on the foot, ankle, and leg, while stabilizing the limb and offering an intimate fit. However, it is envisioned that the orthopedic walker need not be solely limited to the unitary construction.

The walker combines the strength and support of a casting system with the adjustability of an orthopedic walker. However, due to the use of a semi-rigid body material, the walker may be advantageously manufactured with a unitary form construction or of a single part construction. The simplified construction enhances ease and comfort of use and offers a more lightweight structure.

Although the embodiments of the disclosure are suitable for supporting and stabilizing anatomical portions of many users having various anatomical shapes and sizes, the embodiments of the disclosure may also be dimensioned to accommodate different types, shapes, and sizes of anatomical portions. The walker may be an off-the-shelf product accommodating general sizes and shapes of the lower limb and feet or may be readily custom fabricated.

It will be understood that, unless a term is defined in this disclosure to possess a described meaning, there is no intent to limit the meaning of such term, either expressly or indirectly, beyond its plain or ordinary meaning.

While the foregoing embodiments have been described and shown, alternatives and modifications of these embodiments, such as those suggested by others, may be made to fall within the disclosure. While the orthopedic walker has been described in combination with a shape conforming to a lower leg and foot, it will be understood that the principles described may be extended to other types of orthopedic devices and/or for other limbs or body portions For ease of understanding the disclosed embodiments of an orthopedic walker, the front or anterior, and rear or posterior portions of the orthopedic walker are described independently. The anterior and posterior portions are defined by a frontal or coronal plane, $F_p$, as depicted in FIG. 17A. The anterior and posterior portions of the orthopedic walker function together to form a supporting and stabilizing boot that encompasses the anatomical portions of the user.

For some embodiments, the lateral and medial portions of the orthopedic walker are described independently. The lateral and medial portions are defined by a median or sagittal plane, $M_p$, as depicted in FIG. 17A. The lateral and medial portions of the orthopedic walker function together to form a supporting and stabilizing boot that encompasses the anatomical portions of the user. In the instance when the orthopedic walker is universal or generally symmetric for both right and left legs and feet, the sides of the orthopedic walker $S_I$, $S_{II}$, are simply divided by the median plane, as shown in at least FIG. 17A.

The term "posterior" also has its ordinary meaning and refers to a location that is behind or to the rear of another location. The term "anterior" has its ordinary meaning and refers to a location ahead of or to the front of another location. The term "medial" has its ordinary meaning and refers to a location near the median plane of a body, such as the inside of a foot. The term "lateral" has its ordinary meaning and refers to a location farther from the median plane of a body, such as the outside of a foot.

The term "distal" has its ordinary meaning and refers to a location farther from the point of attachment of a limb. The term "proximal" has its ordinary meaning and refers to a location closer to the point of attachment of a limb. However, a structure can be proximal or distal in relation to another point of reference. A knee is distal to an upper leg but proximal to the lower leg, however in the context of the orthopedic walker the knee is used as a frame of reference such that proximal $P_r$ is closer to the knee and whereas distal $D_i$ is farther from the knee.

The terms "rigid," "semi-rigid," and "compressible" may distinguish characteristics of portions of certain features of the orthopedic walker. The term "rigid" should denote that an element of the device is devoid of flexibility. Within the context of support members or shells that are "rigid," it should indicate that they do not lose their overall shape when force is applied, and they may break if bent with enough force.

As for the term "semi-rigid," this term is generally used to connote properties of support members that provide support and are free-standing; however, such support members have some degree of flexibility or resiliency and may continuously deform when appropriate force is applied. The term "compressible" may generally qualify such structural features as being capable of being reduced in size or volume due to the exertion of force applied to the structural feature. The "expanded" plastic may have a lightweight cellular structure, such as a closed-cell foam, however the expanded plastic may cover a porous material or other generally lightweight or low-density material.

The term "unitary" may generally denote that an element of the walker is continuous in its construction, as opposed to comprising an assemblage of separate and spatially adjustable components. The term "elongate" may generally denote that an element of the walker is longer than it is wide.

A better understanding of different embodiments of the disclosure may be had from the following description read with the accompanying drawings in which like reference characters refer to like elements. While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

B. Description of Embodiments

FIG. 1 shows an anterior view of an orthopedic walker 1 in a closed configuration. The orthopedic walker 1 has a unitary form construction in that the structure is continuous and formed from a same material and arranged to extend about the user without interruption. In the illustrated embodiment, a body 2 of the orthopedic walker 1 consists a single material part.

The body 2 has a shape corresponding to a limb and having a unitary form construction to intimately fit against the user. The body 2 is configured to receive a limb of a user in an open configuration, as illustrated in FIG. 2, and to close about the limb of the user in a closed configuration, as illustrated in FIG. 1. In the closed configuration of FIG. 1, the body 2 may have the general shape of a boot, conforming to the shape of a user's foot and a portion of a user's lower leg, inclusive of the ankle. While in the general shape of a boot, the footprint and bulk of the walker 1 is significantly streamlined as it is contoured to the general shape of a lower leg and foot. Unlike in conventional walkers, both the inner and outer peripheries of the body 2 are substantially form-fitting to the anatomical shape of a lower leg and foot.

The body 2 may be configured to an intended treatment purpose for the user. The height of the body 2 may vary depending on a condition to be treated. The body 2 may have a high top extending up the user's lower leg or may be manufactured or trimmed to have a low top. The walker 1 may be configured in different heights to accommodate the pathologies and indications used for treatment.

Due to the unitary construction of the walker 1, the body 2 may have an open or closed toe portion 9. A closed toe portion may be advantageous over prior art embodiments of a cast, where a closed toe is only possible by tightly wrapping the toe area, and an orthopedic brace, where the toe is left open due to the constraints of a multi-component system. In contrast to the prior art systems, the walker 1 may be configured with a closed toe portion 9 that surrounds and protects but does not tightly wrap the toes of a user, resulting in increased comfort over existing walkers. The closed toe portion 9 offers a protective barrier to the environment without adding significant bulk. The closed toe portion 9 is preferably contoured anatomically to toes and improves gait while the walker 1 is worn compared to conventional walkers, making it easier for the user to walk with the walker 1 donned.

In an alternative embodiment, an open toe configuration (not shown) may be advantageous for providing increased access, space, and/or ventilation to the limb of the user. Advantageously, the body 2 may be configured to the needs of the user, and/or may be cut or otherwise altered to adapt to the needs of the user.

The body 2 may be formed as a single part from a semi-rigid body material. The semi-rigid body material reduces the complexity, cost, and weight of the walker 1. The semi-rigid nature of the body material provides rigid support to the limb and allows the walker 1 to resiliently hold or return to its original shape, while having some degree of flexibility or resiliency to facilitate regular donning and doffing. Preferred materials for forming the body include an expanded polymer such as: EVA, rubber foam, or a closed-cell foam. Alternate polymeric materials may be employed having enough rigidity to intimately support and hold the lower limb and foot, while offering a protective barrier to elements and enabling the body 2 to likewise serve as the sole being subjected to repeated ground strike. The materials for forming the body may also advantageously reduce a body weight of the walker without sacrificing needed robustness.

The semi-rigid body material may be configured to have distinct material properties, including material thickness, densities, etc., according to a preferred treatment and/or stabilization. The semi-rigid body material may be configured to substantially retain a shape of a closed configuration of the body 2. In some embodiments, the semi-rigid body material may be configured such that the body 2 provides compression for securing the body 2 about the limb when no force or pressure is applied to the body 2. A shape of the body 2 may be configured to support a particular area, or to prevent a particular motion of the limb.

The interior of the walker 1 and the body 2 may be defined by two portions, namely an upper receiving section 4 defining an upper or proximal part of the orthopedic walker or boot 1 corresponding to the lower leg, and a lower receiving section 6 defining a lower or distal part of the boot 1 corresponding to the foot of a user. As a preferred material for forming the body 2 is a structural foam, the body 2 may be directly secured against the limb while offering both rigidity and compressive support without discomfort.

A bottom surface 8 of the body 2 may be configured with increased thickness as a sole or may be provided with an outsole. The sole 8 may comprise a region with material properties, such as increased thickness or a non-slip surface, or may comprise an attached outsole. If the sole 8 is formed from the body 2, it may be provided with treads to assist the user when walking or may be substantially smooth to reduce the overall shape and footprint, or a combination of the two. Wedges may be inserted into the walker 1 to provide Achilles tendon support and/or protection.

The form-fitting nature of the walker 1, as it is generally formed as a unitary body, has a more streamlined shape, and is much more contoured to the shape of a human foot than in conventional walkers. The rounded edges 13 extending about the foot portion of the walker 1 exemplify how the walker 1 can be configured more as a structural stocking contoured as or to a human foot, rather than a generic shape. The shape of the walker 1 derives from it being moulded to a shape of a human foot, and has a unitary, circumferential design.

According to the illustrated embodiment of FIG. 1, the body 2 defines at least one opening 10 to facilitate donning and doffing of the orthopedic walker 1. The at least one opening 10 is shown in FIG. 1 as an elongate opening, extending from a proximal portion at an end of the body 2 to a distal portion at a second end of the body 2. The walker 1 defines an opening at the upper receiving section 4 and the lower receiving section 6, enabling a limb such as a foot to be slipped into the walker 1 like a boot. The at least one elongate opening 10 separates the body 2 into first and second sides 12, 14 which join to seal or enclose the lower leg and foot of the user. In an alternative example, the at least one elongate opening 10 may only open the upper receiving section 4, increasing the strength and support provided by the lower receiving section 6.

FIG. 2 illustrates that the at least one elongate opening 10 comprises posterior and anterior elongate openings 10A, 10B separating the first and second sides 12, 14. The elongate openings 10A, 10B may be separately formed and closable relative to one another, such that the posterior opening 10A can be closed independently from the anterior opening 10B.

Both elongate openings 10A, 10B may be closed in a clamshell configuration, being biased by posterior and anterior end portions 25, 27 located at the distal end. In this manner, the distal end of the walker 1 provides the base by which the elongate openings 10A, 10B open to receive the user's lower leg and foot. The elongate openings 10A, 10B may be biased from the distal end, allowing the proximal end of the first and second sides 12, 14 to be articulated to significantly open the limb-receiving portion 15 of the walker 1 in variable sizes to accommodate different sized lower limbs and feet. The material forming the walker 1 is sufficiently resilient to undergo repeated biasing of the first and second sides 12, 14 from the end portions 25, 27.

In the illustrated embodiment, the first side 12 corresponds to a lateral side and the second side 14 corresponds to a medial side, and the first and second sides 12, 14 provide support against lateral or medial movement of the limb. Preferably at least the anterior end portion 27 terminates short of the closed toe portion 29 of the walker 1 to assure protection of the user's toe. In the illustrated example, the at least one opening 10 does not extend into or along the bottom surface 8 of the body 2 (when the bottom surface 8 is arranged to be used as a contact surface), so as not to interfere with any surface contour of the bottom surface 8.

In an alternative embodiment, the at least one elongate opening 10 may be arranged to extend both in longitudinal and transverse directions, to provide increased support in preferred portions of the body 2. At least one opening 10 may be generally defined along the frontal plane of the walker 1 (corresponding to the leg), permitting side entry of the lower leg.

If the walker 1 of FIG. 2 is to be donned by a user, the user need only pull the first side 12 and the second side 14 apart, to expand the limb-receiving region 15 into an opened state for introduction of a limb of the user. When released by the user, the first side 12 and the second side 14 can return to the closed state and enclose the limb.

In any of the embodiments, suitable fasteners may maintain the walker 1 in a closed configuration, which may be defined as the at least one opening 10 being closed or generally closed. Buckles, straps, snaps, hooks, and other means may be located on the walker body 2 in predetermined locations to maintain the first and second sides 12, 14 as being directly or generally adjacent to one another despite being donned by the user. While not limited hereto, it is preferable that the walker 1 forms or is located circumferentially about the user to fully arrest movement of the lower limb during rehabilitation by the user. This may be achieved by intimately securing the walker 1 about the user's injured area and maintaining the limb in a fixed position by at least the fasteners securing the walker body 2 against the user.

The semi-rigid body material may be configured to have a predetermined thickness, density and/or rigidity, such that the body 2 may compress tightly against a limb or against preferred regions of a limb. The semi-rigid body 2 is preferably configured to have a thickness, density, and/or rigidity that remains flexible enough for a user to open the body 2 when introducing a limb. The body 2 may have different thicknesses over its entirety. Side portions corresponding to a frontal plane of the first and second sides 12, 14 may have increased thickness, to provide additional support over other areas of the body 2 that require more restriction of movement.

The body 2 may have an increasing thickness from a proximal end to a distal end, such that the lower receiving section 6 is more rigid than the upper receiving section 4. The body 2 may be configured with increased thickness around affected areas, or in a configuration forming a thicker and more rigid "frame" within the body 2.

In an alternative to the illustrated embodiment of FIG. 2, the orthopedic walker 1 may have a low top configuration, such that a user may insert a limb with or without the at least one opening 10 of the embodiments according to FIG. 1. A low top configuration is understood here to correspond to the understanding of a low top shoe. The length of the body 2 may be made to any necessary length to provide appropriate support to the user.

The material properties of the body 2 may vary to facilitate donning and doffing. A heel-supporting area may be configured with increased elasticity to allow a heel of a user to compress the heel-supporting area during donning. The heel-supporting area could then be pulled up around the heel, or elastically return to its original shape about the heel. The material properties may be modified depending on the location of the material in view of the walker 1 or the structural properties, such as thickness, may likewise be adapted depending on the location in view of the walker 1.

In the example according to FIG. 1, the exterior surface of the body 2 is provided with a plurality of openings 16 configured to ventilate the limb, reduce pressure on a region, and/or reduce the weight of the body 2. In providing or arranging the plurality of openings 16 in the body 2, the benefit of ventilation, reduced pressure and reduced weight must be considered against the potential loss of support or strength provided by the body 2, as understood by one skilled in the art in view of the teachings of this disclosure. The arrangement of the openings 16 may thus be optimized for reducing the weight of the walker 1 without sacrificing support, for example.

The body 2 may be provided with cutting indicia, such that a user or clinician may cut-out or remove portions of the body 2 according to the needs of a user or to adjust the size or weight of the orthopedic walker 1. The body 2 may be simply configured to tightly conform to a limb without contacting a swollen or injured portion that is sensitive to contact. In the same way cutting indicia may be provided on the upper receiving section 4 to adjust the height of the body 1 to a user. In addition to guidance for trimming the length of the walker 1, cut lines may be provided along the body 2, such as with indents or recesses.

As shown in the embodiment of FIG. 2, the at least one elongate opening 10 or the elongate openings 10A, 10B may be defined by a first edge 20 on the first side 12 and a second edge 22 on the second side 14. The first edge 20 may be provided with a receiving recess 21 arranged to receive a protruding part 23 from the second edge 22.

Referring to FIG. 3, a shape of the receiving recess 21 is configured to correspond to a shape of the protruding part 23. The receiving recess 21 and the protruding part 23 may have any suitable shape for connecting the first edge 20 and the second edge 22, such as a J-hook shape. The surface of the receiving recess 21 and the protruding part 23 may further be provided with a friction enhancing texture to strengthen a locking of the first edge 20 and the second edge 22. In an alternative embodiment, the first edge 20 and the second edge 22 may each be provided with at least one receiving recess 21 and at least one protruding part 23 to lock in an alternating, zipper-like method.

To increase the comfort and fit of the body 2 around a limb, an interior surface of the limb receiving region 15 may be provided with a textured surface or a plurality of protrusions. The textured surface or the plurality of protrusions may be arranged to allow for an increased friction against a movement of a limb, or to provide a lower density cushion for the limb.

FIGS. 4 and 5 show another embodiment of a walker 17 having a bottom surface 28 provided with a recessed portion 30 to facilitate donning and doffing of the walker 17. The recessed portion 30 may be configured to increase a variable distance d between the first and second sides 18, 19 of the walker 17 along at least one opening, to provide a larger opening for insertion of the limb of the user.

In the illustrated example, the recessed portion 30 is shown extending from a posterior end 32 to an anterior end 34 of the bottom surface 28. The recessed portion 30 acts as a joint or vertex for the separation of lateral and medial sides of the walker. In this way the walker body may be advantageously opened and applied to the limb of the user without requiring the user to move or manipulate the limb, for example when the user is lying in a hospital bed.

Variations in placement and configuration of the recessed portion 30 and the at least one opening are possible, as understood by one of ordinary skill in the art from the detailed description of the exemplary embodiments.

Figure 6B:
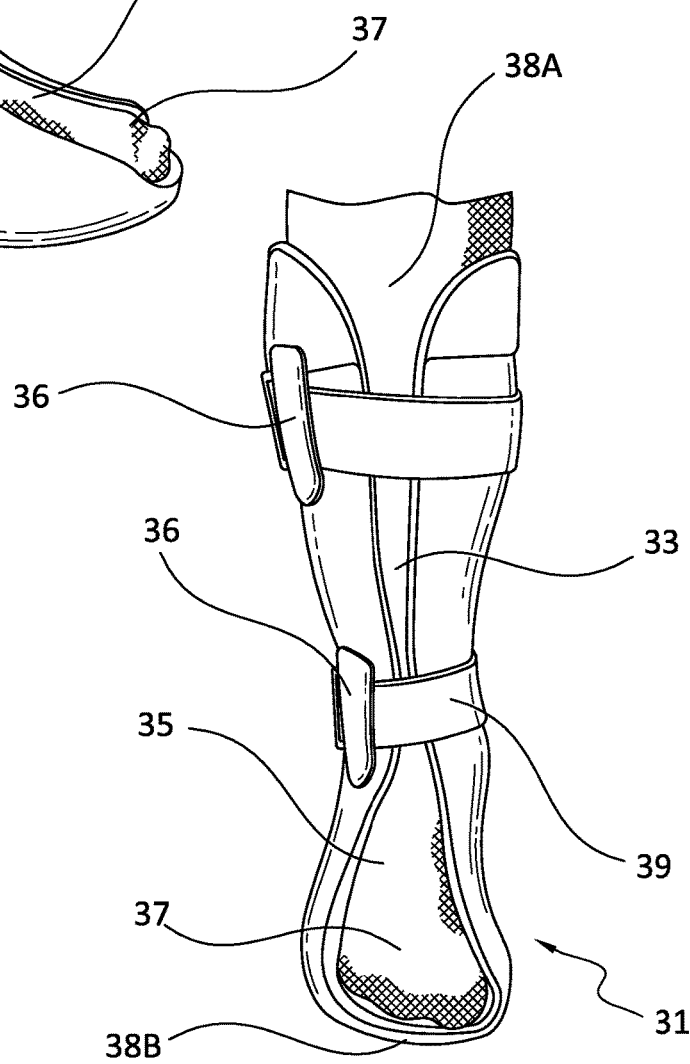
FIG. 6B is a front elevational view of the embodiment of FIG. 6A.

FIGS. 6A and 6B represent exemplary embodiments of a walker 31 having integrated strap retainers 36A, 36B for supporting circumferential straps 39A, 39B. The strap retainers 36A, 36B may comprise at least one channel, hole, slot, slit, or opening formed by the walker body for permitting insertion of the straps 39A, 39B to close the walker 31 and/or be firmly secured about the walker 31.

The walker 31 also represents a configuration that can easily accommodate different sized feet and lower legs, while offering access to the toe by forming a toe section 37 that is open. A dorsal portion 35 of the walker 31 may likewise be open with the toe section 37, to offer relief at the dorsal portion 35. The walker 31 preferably forms a continuous opening between the proximal and distal ends 38A, 38B, and is closed on the anterior side by the straps 39A, 39B. The posterior side of the walker 31 may be closed without an opening, or may include a posterior opening, much as in the other embodiments. If the walker 31 is only provided with an anterior opening 33, the material of the walker 31 is sufficiently resilient to adjust to opening about the anterior side of the walker 31 to accommodate the lower leg and foot, but when the straps 39A, 39B are tensioned, the walker 31 firmly and rigidly inhibits movement of the ankle and foot.

Figure 7A:
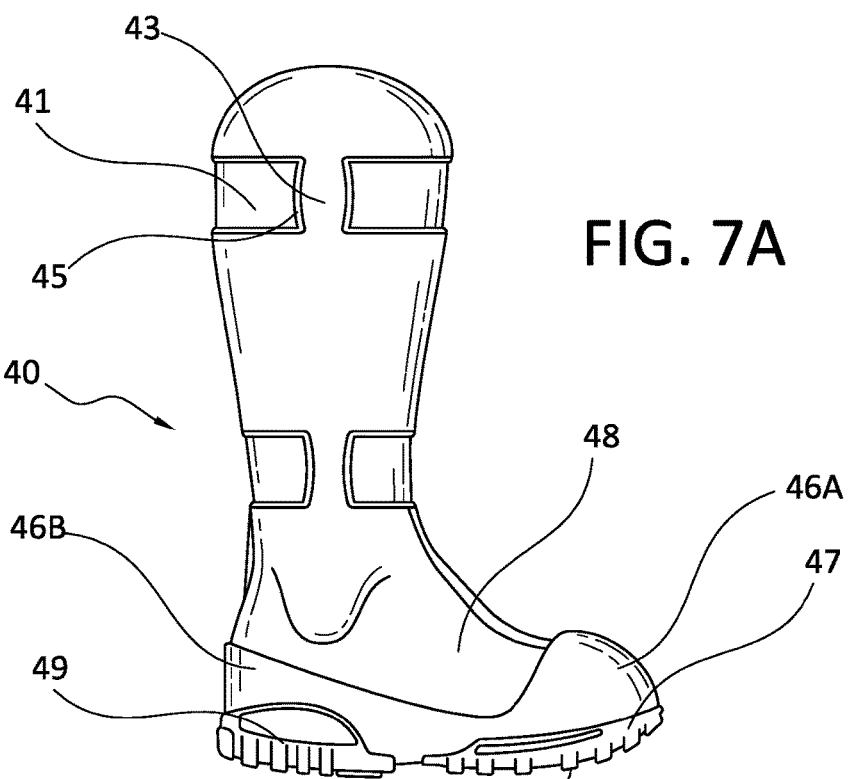
FIG. 7A is a side elevational view of another embodiment of an orthopedic walker.
Figure 7B:
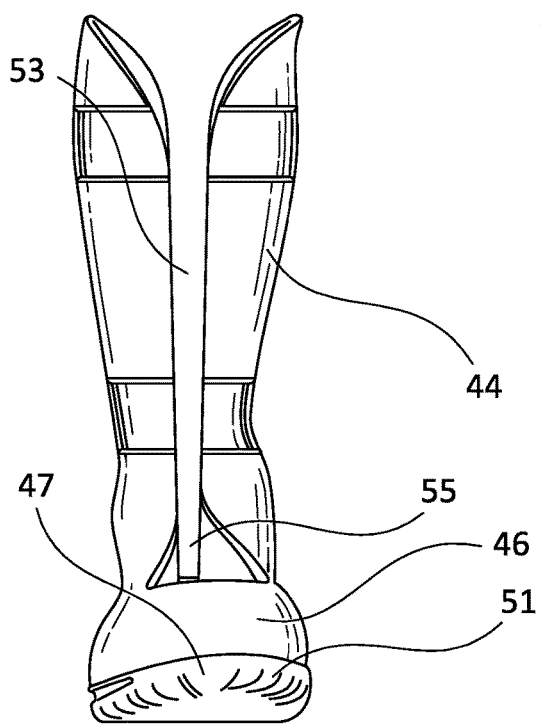
FIG. 7B is a front elevational view of the embodiment of FIG. 7A.
Figure 7C:
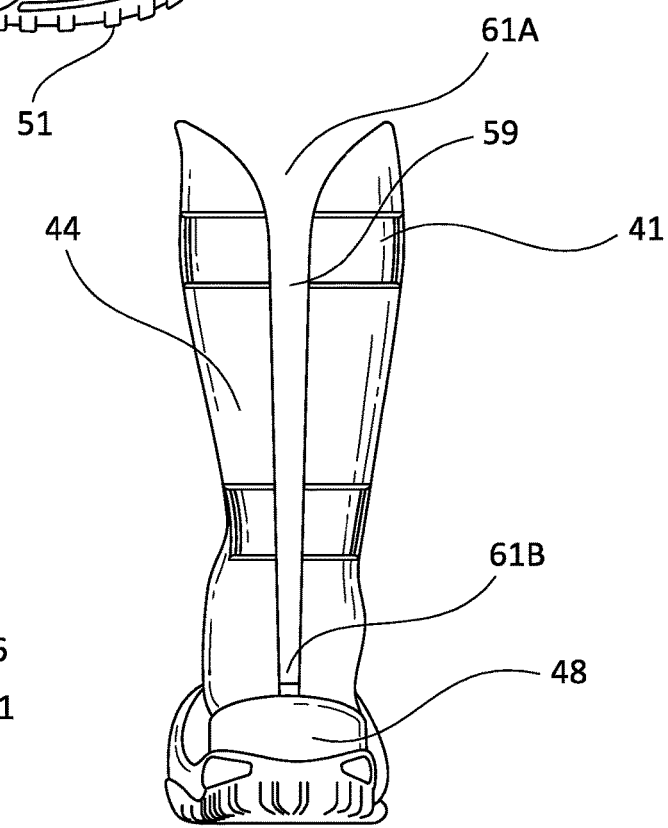
FIG. 7C is a rear elevational view of the embodiment of FIG. 7A.

FIGS. 7A-7C exemplify another walker 40 having differently formed sections, preferably from a unitary construction, that may be considered to have been moulded simultaneously, or post-fabricated with differently formed sections. The differently formed sections may be structurally arranged differently, or may be formed with different properties, or both.

The walker 40 comprises a body 44 that defines a recess portion 41 for receiving a strap (not shown). The recess 41 extends generally circumferentially about the walker 40 to accommodate a strap that is likewise preferably secured circumferentially about the walker 40 to close anterior and posterior openings 53, 59. The walker 40 forms strap retainers 43, as in the preceding embodiment, to maintain the straps within the recess 41. The strap retainer 43 defines a slot 45 through which the strap may extend.

The walker 40 defines bolsters 46A, 46B at the distal end proximate to the sole 47. The bolsters 46A, 46B may be thickened regions of the walker 40, exhibiting a thickness greater than neighbouring section 48, which may exhibit greater flexibility. The bolsters 46A, 46B may be formed from a different material composition, may exhibit surface roughness, or may possess other features to enhance its toughness compared to the neighbouring section 48 since the bolsters 46A, 46B may be subjected to more wear and tear.

The sole 47 may be formed from a tougher material than other portions of the walker 40 and can have tread features 51 to improve traction while the user is walking. Upper portions 49 of the sole 47 may also have features to enhance durability and increase the structure of the sole 47 to provide enough to the user's foot. In certain embodiments, the sole 47 may be formed of a material that provides shock-absorbing effects and/or energy return to the user.

The anterior and posterior openings 53, 59 may be formed differently from one another to facilitate donning. The anterior opening 53 has a dorsal opening 55 with a larger opening section than in other parts of the anterior opening 53, which aids in placing the foot within the walker 40. The posterior opening 59 flares at a proximal end 61A to reflect the normal anatomy of a lower leg, such as at the calf. The posterior opening 59 tapers by decreasing width toward a distal end 61B, which likewise reflects the normally anatomy of an Achilles tendon. With both the anterior and posterior openings 53, 59, both may be closed, at least in part, by the aforementioned straps, with recesses 41 placed appropriately to aid in closure of the walker 40.

Figure 8A:
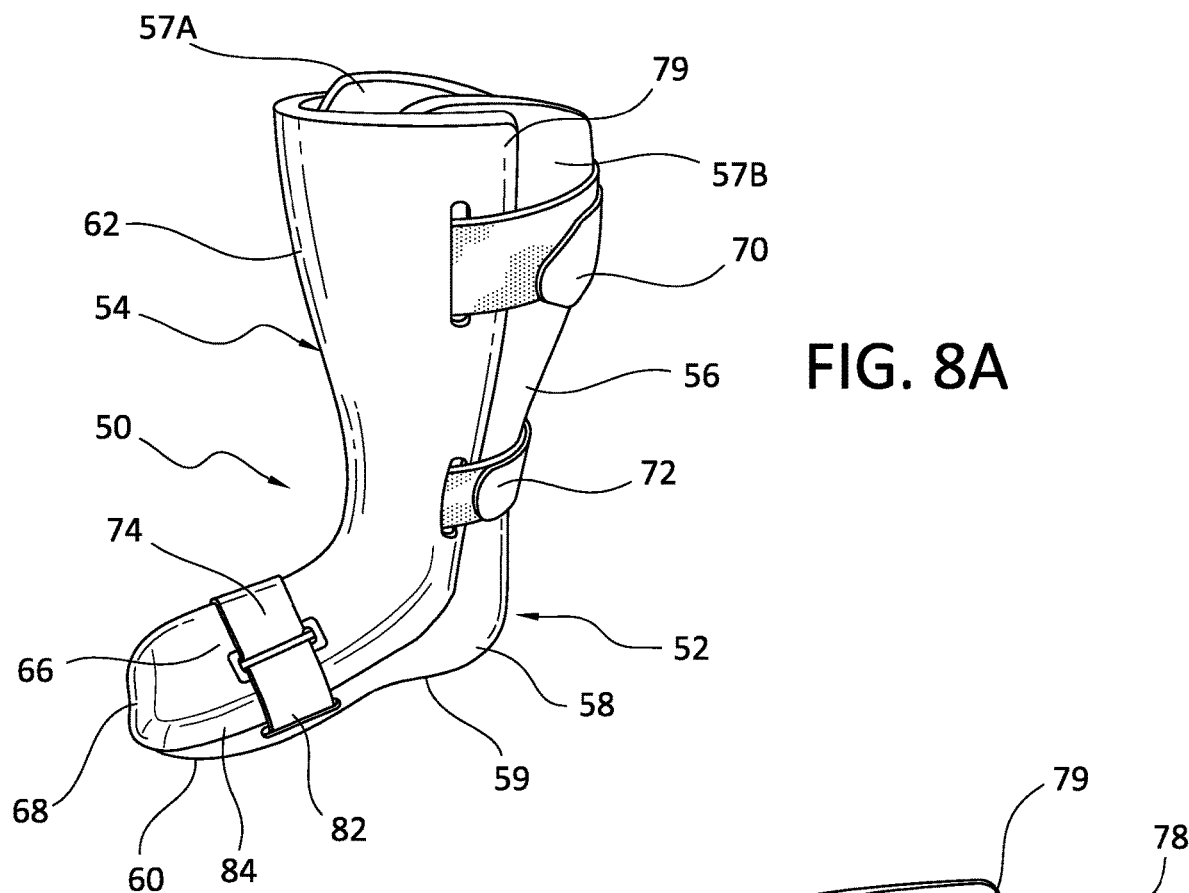
FIG. 8A is a perspective view of another embodiment of an orthopedic walker.
Figure 8B:
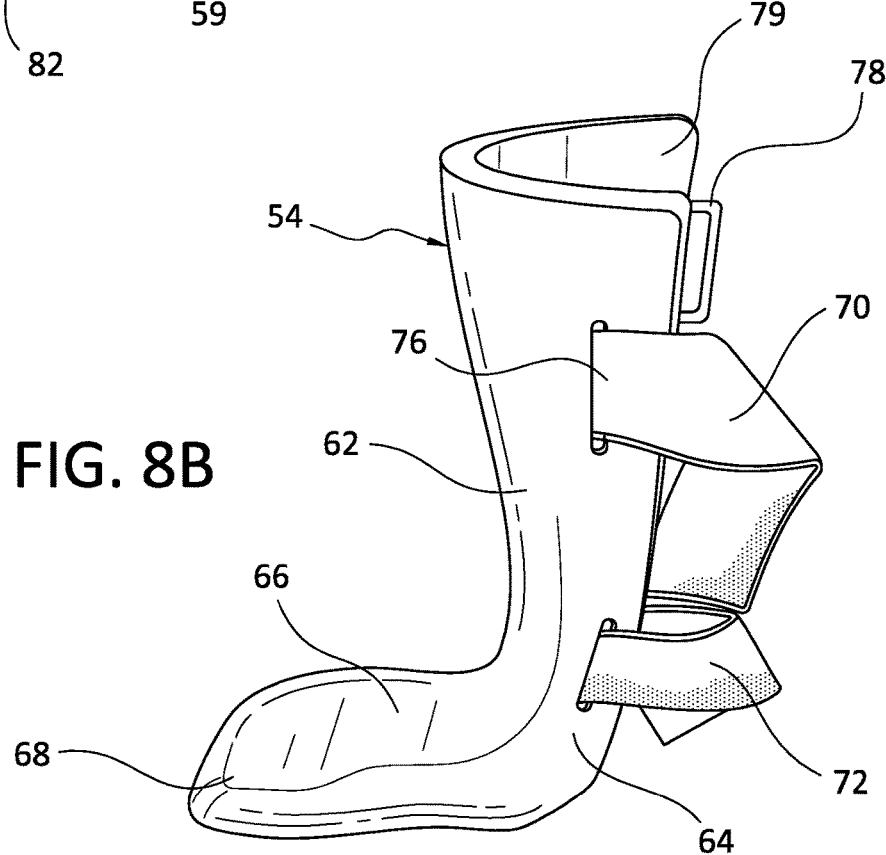
FIG. 8B is a perspective view of a dorsal/anterior component of the embodiment of FIG. 8A.

FIGS. 8A and 8B show another embodiment of a walker 50 having multiple components, as in posterior and anterior components 52, 54 separable from one another. Each of the components 52, 54, however, are preferably unitary in structure, and corresponding fit with one another.

The posterior component 52 comprises leg and ankle portions 56, 58 corresponding to the posterior of the leg, and defines a foot portion 60. The leg portion 56 defines proximal wings 57A, 57B arranged to extend anteriorly. The foot portion 60 may have a sole portion 59 defined similarly to any of the other embodiments described herein. The foot portion 60 forms a foot bed 84 for receiving the user's foot.

The anterior component 54 is arranged extend over the posterior component 52, and has leg, ankle and dorsal portions 62, 64, 66 that overlap the leg, ankle and foot portions 56, 58, 60 of the posterior component 52, to generally completely enclose the lower leg and foot. For example, a peripheral edge 79 of the posterior component 54 extends and overlaps the proximal wings 57A, 57B. The anterior component 54 preferably defines a closed toe portion 68 which encases a toe portion of the foot portion 60.

A configuration of straps 70, 72, 74 is secured to the posterior and anterior components 52, 54 to draw the posterior and anterior components 52, 54 toward one another. The anterior component 54 may form a slot 76 about which the strap 70 is secured along the peripheral edge 79 on one side of the anterior component 54, and couples or loops about a corresponding slot or bracket 78 integrated with the anterior component 54 whereby the bracket 78 is formed from a different material from the anterior component 54, or formed by the anterior component 54, such as a bracket 78 molded unitarily from the same material as the anterior component 54.

The foot portion 60 of the posterior component 52 may form a slot 82 in the thickness thereof, through which the strap 74 feeds to pull the anterior component 54 toward the foot portion 60 of the posterior component 52. The configuration of straps 70, 72, 74 is not limited to those illustrated and described, and other forms applying or adopting these configurations are envisioned by the disclosure.

Figure 9:
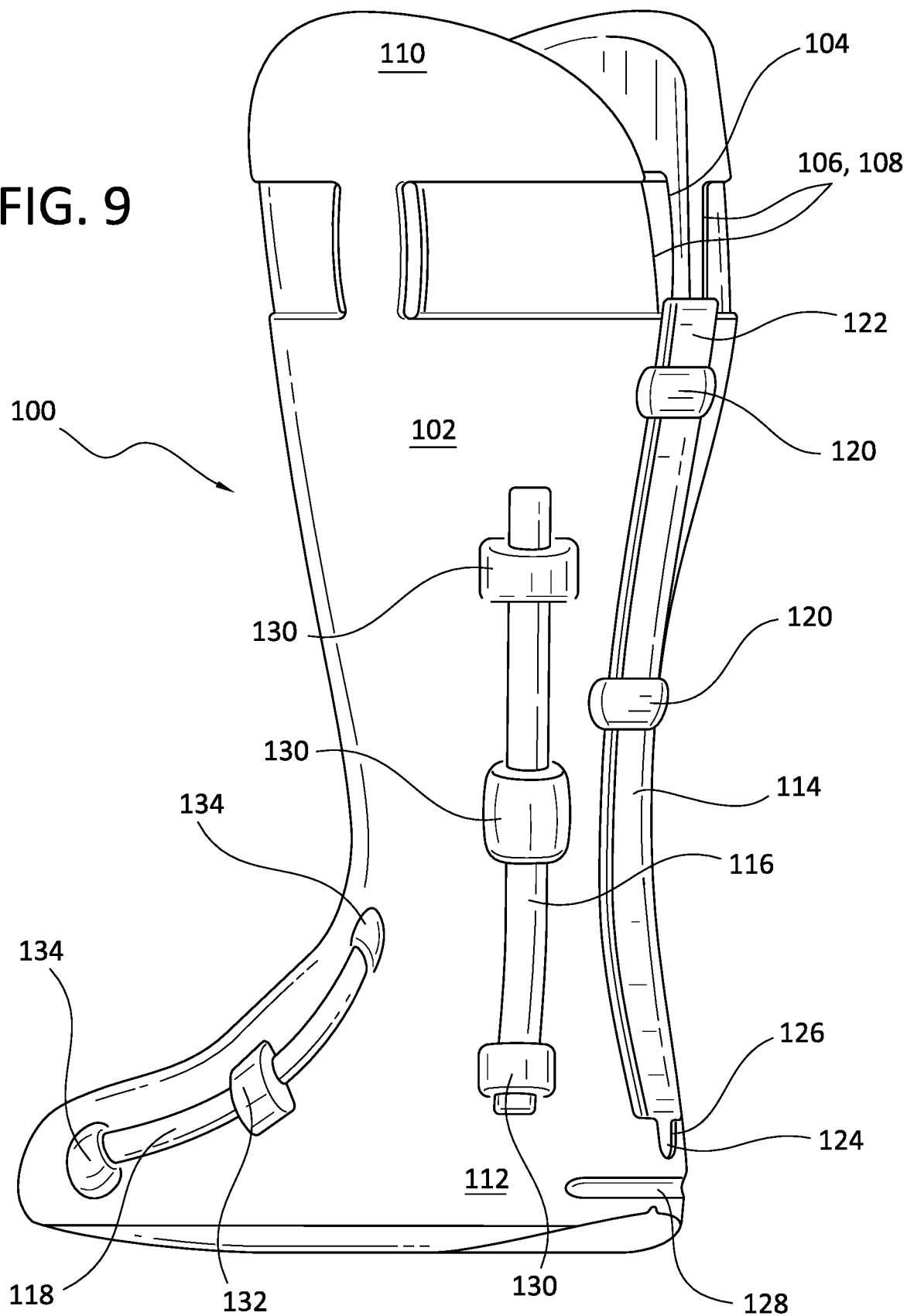
FIG. 9 is a perspective view of another embodiment of an orthopedic walker.

FIG. 9 exemplifies how any of the embodiments of a walker may be provided with reinforcement elements. Specifically, a walker 100 includes a body 102 forming an opening 104 along at least a posterior side of the walker 100, separating first and second proximal portions 106, 108 of the body 102. The first and second proximal portions 106, 108 may be drawn together by a strapping configuration as depicted in FIGS. 6A-7C.

The posterior side of the walker 100 includes an elongate reinforcement element 114 disposed from the proximal end 110 to the distal end 112 of the body 102. The reinforcement element 114 may extend below the opening 104 to just above a heel notch 128. The heel notch 128 may be provided as a pressure relief feature to accommodate heel strike of the walker 100. The reinforcement element 114 is arranged for being selectively inserted through retainers 120 formed by the walker body 102, with a distal end 124 of the reinforcement element 114 being received at a distal seat 126 formed by the body 102. The proximal end 122 of the reinforcement element 114 may extend freely or be otherwise accessible so the reinforcement element 114 may be removed.

The walker 100 may have lateral/medial reinforcement elements 116 on opposed sides of the body 102 to increase walker strength, particularly about an ankle portion of the body 102. Retainers 130 may be formed by the body 102 or otherwise attached to the body 102 to permit the lateral/medial supports 116 to be selectively added to the walker 100. Likewise, fore/aft reinforcement elements 118 may be selectively added to lateral and medial sides of the walker 100 and retained by retainers 132, and/or received by end holders 134.

The reinforcement elements 114, 116, 118 may be selected among a plurality of different types of reinforcement elements having different stiffnesses and other useful properties. Some reinforcement elements may be more rigid than other reinforcement elements. An example includes reinforcement elements constructed from malleable aluminum that can be adapted to the anatomy of a specific user. The length of the reinforcement elements 114, 116, 118 may be modified as considered necessary to a user's requirements. By providing reinforcement elements 114, 116, 132 according to embodiments of the disclosure, the walker 100 may advantageously comprise a body 102 that is lighter in weight and bulk compared to existing devices without sacrificing needed strength and support.

Other benefits or functions offered by the reinforcement elements 114, 116, 132 may include range-of-motion control, energy return, and/or improved stability in particular directions or regions. For example, a reinforcement element may be provided proximate a malleolus of a user and on an indicate side of the user's leg to immobilize and support the user.

Figure 10A:
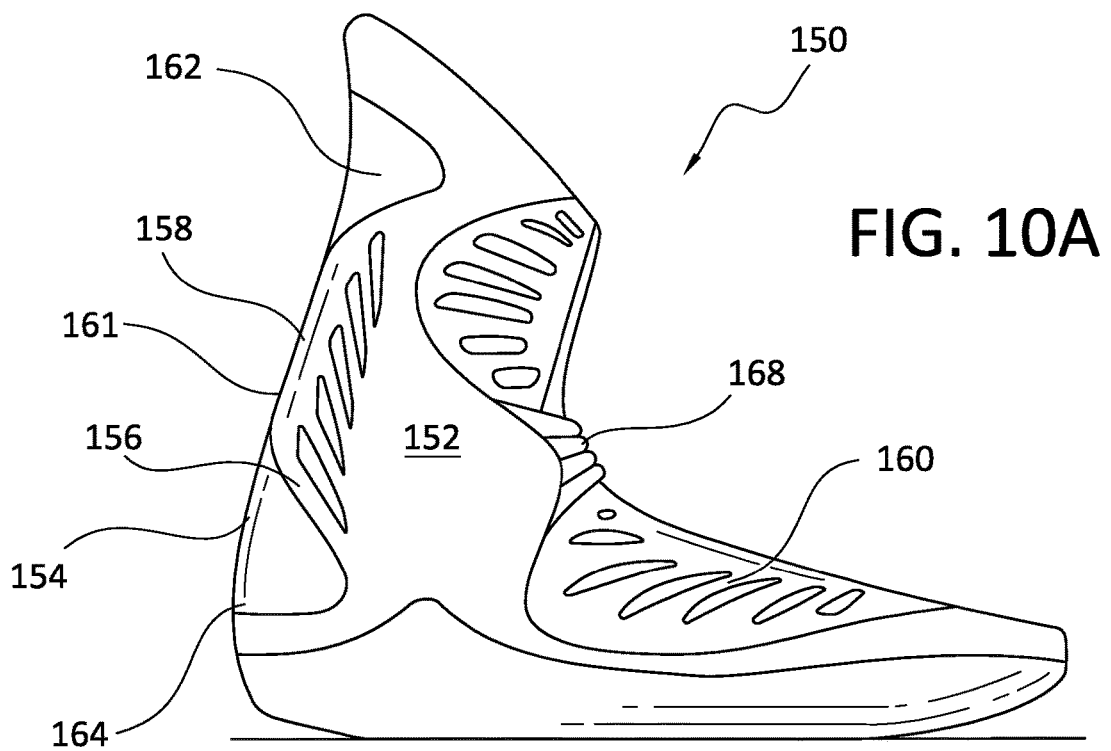
FIG. 10A is a side elevational view of another embodiment of an orthopedic walker.
Figures 10B, 10C:
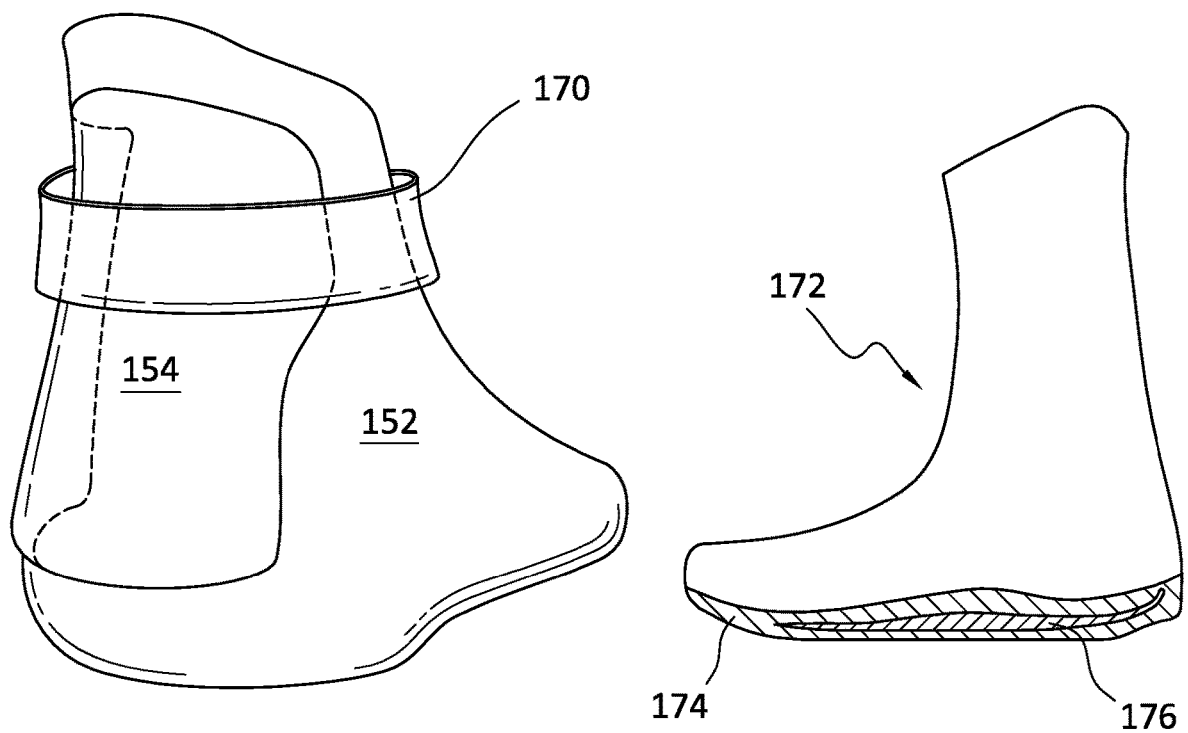
FIG. 10B is a rear perspective view of the embodiment of FIG. 10A.
FIG. 10C is a side elevational view of another embodiment of an orthopedic walker.

FIGS. 10A and 10B illustrate another walker 150 having a removable and contourable reinforcement element 154. While the reinforcement elements 114, 116, 118 are generally rods or bars, the reinforcement element 154 may define a specific, complex shape received by a corresponding walker recess 156 formed by the walker body 152. The reinforcement element 154 may press fit into the recess 156 or adhere thereto by other known fasteners such as an adhesive or removable fastener such as hook and loop. The reinforcement element 154 may be secured to the body 152 by a circumferential strap 170.

In the illustrated example, the posterior portion 158 of the walker 150 receives the reinforcement element 154 comprising proximal wings 162 and distal wings 164 that provide lateral and medial support to the walker 150 in addition to posterior support provided between the proximal and distal wings 164 by a posterior portion 161 of the reinforcement element 154. The reinforcement element 154 may be selectively added to the body 152 depending on the user's requirements for support.

The embodiment of FIG. 10A also exemplifies how the walker 150 may have a dorsal shell 160 with edge contours corresponding to edge contours of the body 152. The dorsal shell 160 may have one side connected to the body 152 by a living hinge or may be completely separable from the body 152. The dorsal shell 160 may be formed from the same material as the body 152. A strap 168 may be provided which extends over the dorsal shell 160 and is connected to the body 152, which retains the dorsal shell 160 relative to the body 152.

FIG. 10C shows how an orthopedic walker 172 may have a footbed 174 (or other locations and sections) reinforced with a reinforcing footplate 176 or other suitable inserts. The reinforcing footplate 176 may be constructed from many structural materials, having greater strength or resiliency than the material forming the body of the orthopedic walker 172.

FIG. 10D shows how an orthopedic walker 178 may have a body 180 reinforced by material thickness or other structural features, such as supplementary material sections 181, 182, 183, 184 formed from material having different properties from the body, 180 and provided in anatomically distinguishable sections. The reinforcement feature 181 may correspond to the foot, whereas reinforcement feature 182 may correspond to the malleolus or ankle. The reinforcement feature 183 may extend posteriorly along the body to inhibit flexibility, and the reinforcement feature 184 may underlie the foot.

While not limiting, in certain embodiments of the disclosure the malleolus-corresponding reinforcement feature 182 may be provided with increased thickness and/or decreased elasticity relative to the body 180 to provide improved stability and/or immobilization to the user's ankle. Alternatively, or in addition, the reinforcement feature 183 may provide a different elasticity than the body 180 for controlling a range of motion of the foot. It will be understood that alternative arrangements are contemplated.

FIG. 10E exemplifies an orthopedic walker 185 having a reinforcement feature 186 intended to be contoured about or along a periphery of at least part of an ankle. An indicator or indicia 187 may denote a region for modification of the orthopedic walker 185, such as a cut-out area 188 for removing material for wound safety, treatment, pressure relief, ventilation, weight reduction, or other purposes. The indicia 187 may be formed from the body 180 and can comprise protruding or recessed portions of the body 180. In an embodiment, the indicia 187 and/or cut-out area 188 may be provided on an interior surface of the orthopedic walker 185.

FIGS. 10F-10G show an orthopedic walker 189 wherein the edge portions 190 have a thickness the relative to a thickness $t_b$ of the body 180. The edge portions 190 may have a taper 191 either formed along an inner side (as depicted) or an outer side of the body 180. The thinned edge portions 190 offer a more flexible edge to the orthopedic walker 189 to reduce pressure portions or points, and/or permit the clinician to trim the body 180 according to the anatomy of the user.

FIG. 10H exemplifies how the orthopedic walker 192 can have a cut-out 193 for modification of the body 180. In the depicted illustration, the cut-out 193 is provided for removing material about an Achilles region 194 of the body 180 to offer relief. The cut-out 193 may be formed as reduced material portions that can remain intact as part of the body 180 if it is not desired for removal.

Figure 11A:
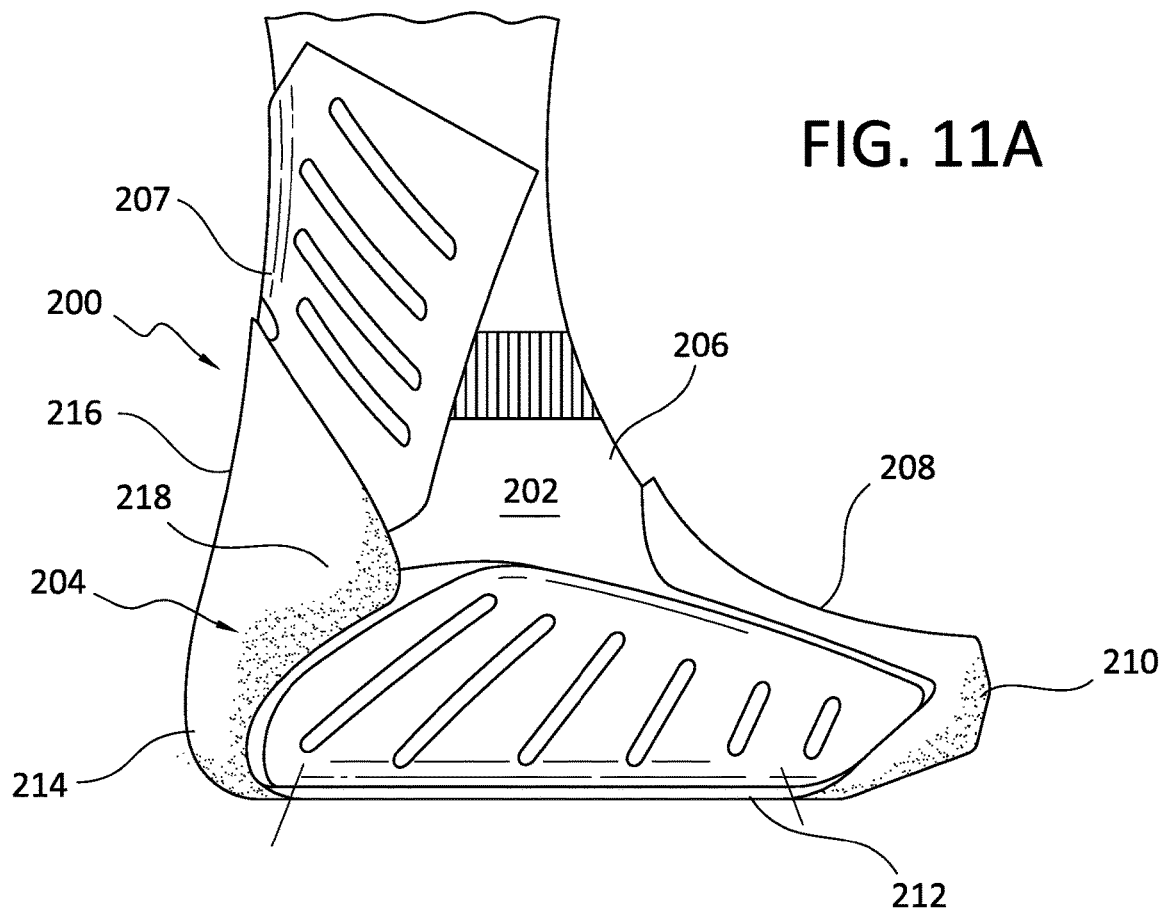
FIG. 11A is a side elevational view of another embodiment of an orthopedic walker.
Figure 11B:
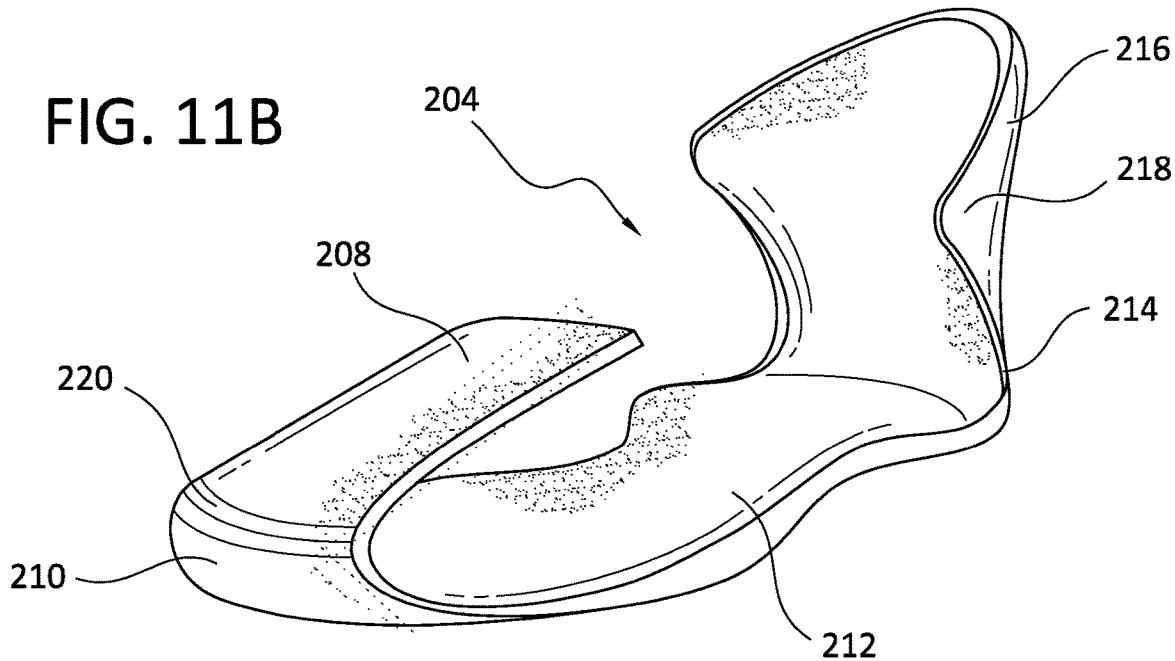
FIG. 11B is a front perspective view of a reinforcement component of the embodiment of FIG. 11A.

FIGS. 11A and 11B show a walker 200 comprising another example of a reinforcement element 204 that may be added to a walker body 202, to define and provide support for a sole of the walker 200. In this manner, the reinforcement element 204 may be substantially stiffer and tougher than the material forming the body 202. The reinforcement element 204 may extend from a dorsal portion 206 underneath the body 202 to a posterior portion 207.

This example of a reinforcement element 204 includes a dorsal portion 208, a toe portion 210, a sole portion 212, a heel portion 214, and a posterior portion 216. The reinforcement element 204 may also have wings 218 that wrap about the heel, for example about medial and lateral sides, and posterior portions 214, 216.

As seen in FIG. 11B, the reinforcement element 204 may be modified according to areas of the walker 200 whereat reinforcement is needed and is not limited to having all the portions. The reinforcement element 204 may have hinged sections 220, such as a living hinge, for example between the toe portion 210 and the dorsal portion 208 to facilitate bending, while maintaining a continuously formed reinforcement element 204. The reinforcement element 204 is not limited to being continuously formed but may comprise a plurality of parts selectively placed at desired portions of the body 202. The sections/portions of the reinforcement element 204 may have different materials or properties at different locations.

Figure 11C:
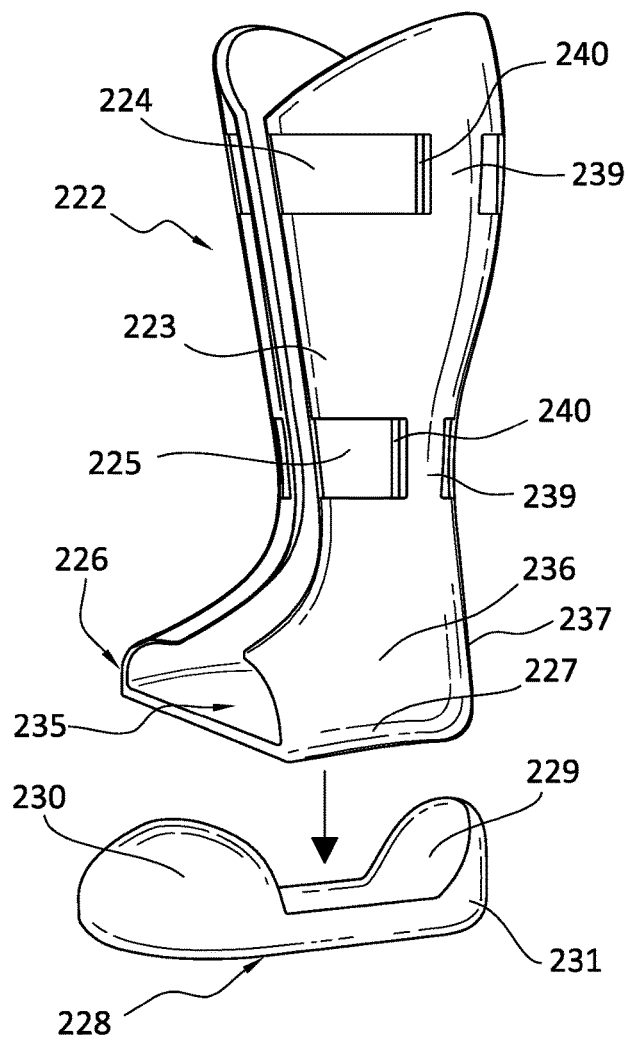
FIG. 11C is a schematic view exemplifying placing a sole component to an orthopedic walker.
Figure 11D:
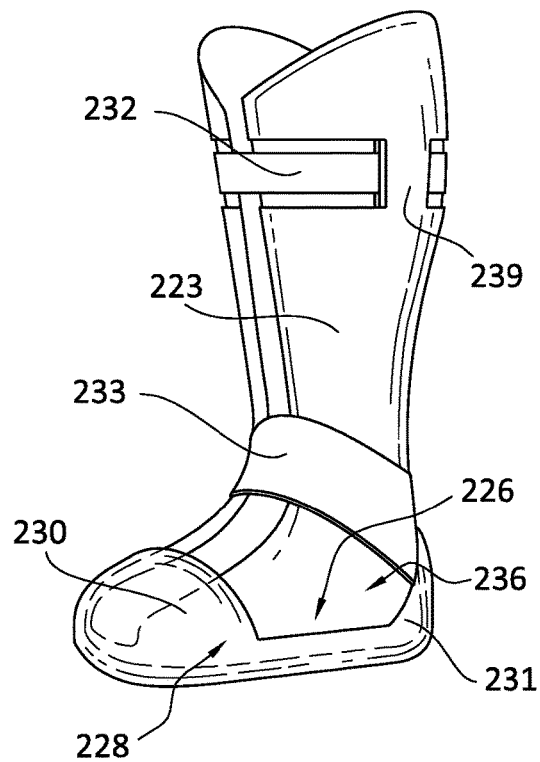
FIG. 11D is a perspective view of the orthopedic walker of FIG. 11C with the sole component installed.

FIGS. 11C and 11D exemplify how a sole component 228 can be added to a footbed 226 of an orthopedic walker 222 having a body 223. The footbed 226 defines an outer surface 227 extending at least into part of the lower receiving portion 236. The footbed 226 may define an open anterior region 235 generally corresponding to where toes of a foot may extend. The sole component 228 may have a closed anterior region 230 arranged to fittingly engage the anterior side of the footbed 226 to close the open anterior region 235.

The sole component has a cavity 229 wherein the footbed 226 may be inserted, and a closed posterior region 231 that extends about a posterior region 237 of the footbed 226 and may additionally extend to the lower receiving section 236. The sole component 228 may have elasticity so the closed anterior and posterior regions 230, 231 can elasticity extend to fittingly and snugly engage the body 223, as shown in FIG. 11D. The sole component 228 may form a tread or other suitable surface to provide traction to the orthopedic walker 222. The sole component 228 can serve as a strap to retain a user's foot in the body 223 at the footbed 226 and lower receiving section 236.

FIGS. 11C and 11D also show how the body 223 can form recesses 224, 225 for retaining straps 232, 233 at a predetermined location to prevent migration of the straps 232, 233 over the surface of the body 223. The body 223 may form retainers 239 having slots 240 through which the straps 232, 233 extend to offer yet further retention means for the straps 232, 233.

The sole component 228 may attach to the walker body 223 by any suitable means, including but not limited to magnets, zippers, hooks and corresponding loops, hook-and-loop fastener, straps, click-on components, or otherwise. The sole component 228 and the outer surface 227 of the footbed 226 may comprise corresponding structures (not shown) that provide engagement and support between the sole component 228 and the walker body 223 in an engagement configuration. The corresponding structures may comprise mating ribs that provide structural support but are arranged to mate such that the profile of the combined walker body 223 and sole component 228 may have a minimal profile.

In embodiments, the sole component 228 may have a wider configuration than the footbed 226 for pressure distribution and optimized traction over a walking surface. In other embodiments, the sole component 228 may comprise pull loops for ease of donning and doffing the sole component 228. Whereas in embodiments a single size or version of the walker 222 may be provided (as the walker 222 may accommodate differently sized users), different sizes of sole component 228 may be provided and interchanged with the walker 222.

In other embodiments, the walker 222 and the sole component 228 may be arranged in thickness or construction to minimize heel-height discrepancy between the walker 222 and the user's unaffected foot. For example, the sole component 228 may be arranged to have a height or thickness like a shoe worn outdoors, whereas the footbed 226 may have a reduced thickness such that heel height is minimized indoors (such as if the user is not wearing a shoe on the unaffected foot).

Figure 12A:
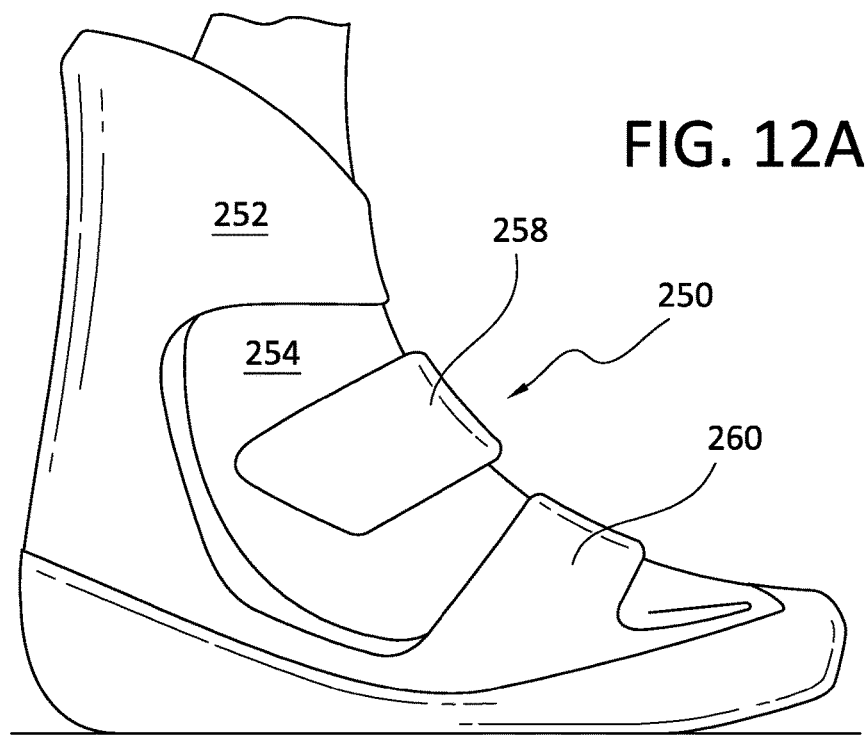
FIG. 12A is a side elevational view of another embodiment of an orthopedic walker.
Figure 12B:
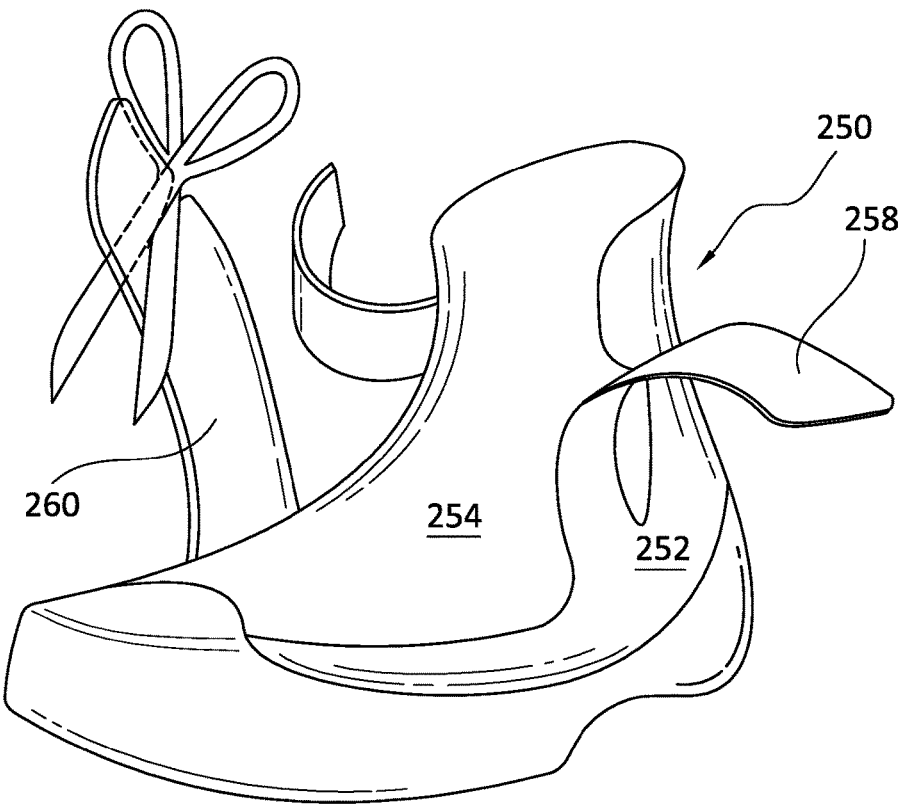
FIG. 12B is a schematic front perspective view of the embodiment of FIG. 12A being adjusted.

FIGS. 12A and 12B exemplify a walker 250 having different regions of breathability. A walker body 252 forms a frame to the walker 250, particularly along the posterior, and medial and lateral sides, and along the sole or foot bed. In the areas outside of the walker body 252, a textile, foam or other flexible and breathable material 254 may be provided. The body 252 may have strap segments 258 placeable over the breathable material 254 to tighten the walker 250 about the user. Frame elements or additional straps 260 of the walker body 252 may overlap the breathable material 254, thereby providing improved structure to the body 252.

FIG. 12B specifically illustrates how the strap segments 258, 260 may be trimmable to an appropriate length for the user. These strap segments 258, 260 may be formed from the same material and directly from the body 252.

FIG. 13 shows another embodiment including a walker 300 having a body 302, which a breathable material 304 bridging areas within the body 302. The walker 300 has a toe portion 306 either formed from the body 302 or formed from a separate material secured to the body 302. The body 302 defines a strap 308 unitary and continuous with the body 302. The strap 308 forms a plurality of slots 312 arranged to receive a fastener 310 for securing to at least one of a plurality of slots 314 formed by the body 302.

The fastener 310 includes a base portion 316 retained by at least one of the slots 312 of the strap 308. The fastener 310 rests within at least one of the slots 312 by a groove 322, and a head portion 320 of the fastener 310 protrudes from the strap 308 to engage the at least one slot 314 of the body 302. The fastener 310 preferably is formed from a harder material than the material forming the body 302, so that as the head portion 320 is pressed into the at least one slot 314, the material about the at least one slot 314 may slightly yield to accommodate the fastener 310. The fastener 310 structure may be formed from the material forming the strap 308 and body 302.

FIGS. 14A and 14B show another embodiment of a walker 350 wherein at least one strap 358 is separately connected to a body 352 of the walker 350. The body 352 defines an edge 354 that defines a slot 356 through which a strap 358 secures. The strap 358 may form a boss 360 with a size larger than the slot 356 to retain the strap 358 with the body 352.

Figure 15A:
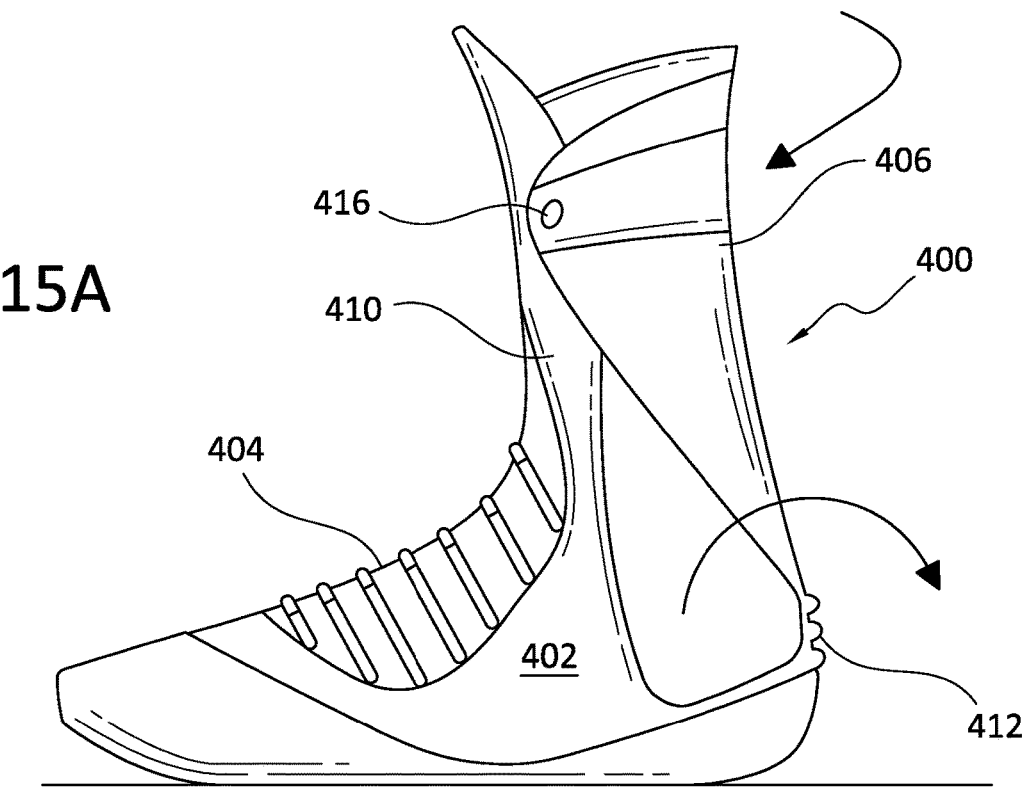
FIG. 15A is a side elevational view of another embodiment of an orthopedic walker in a closed configuration.
Figure 15B:
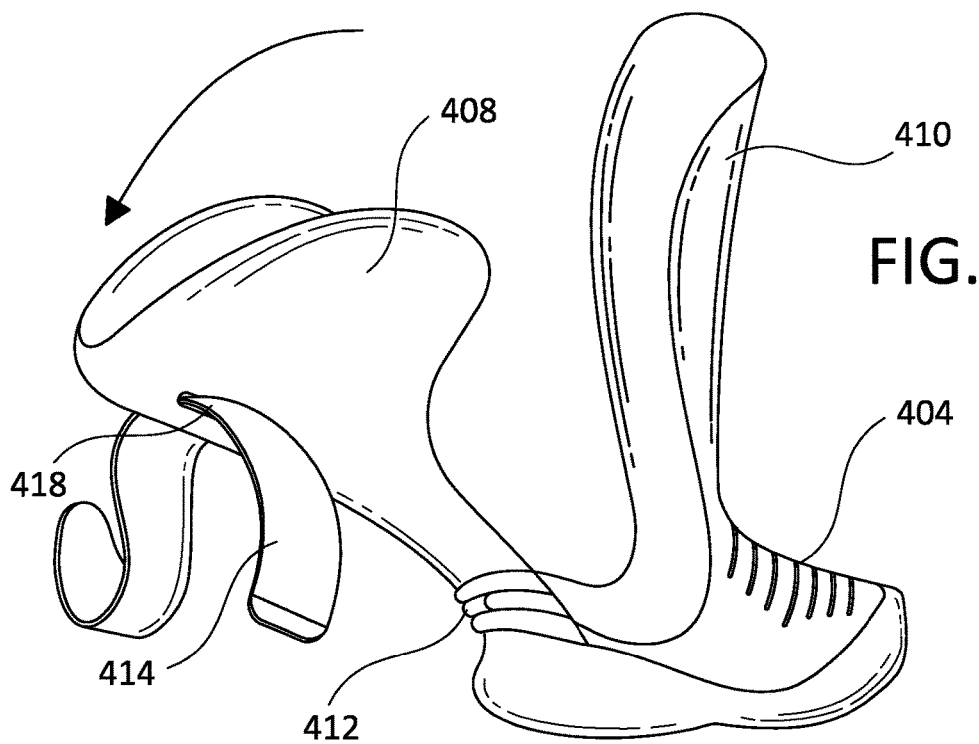
FIG. 15B is a rear perspective view of the embodiment of FIG. 15A in an open configuration.

FIGS. 15A and 15B exemplify another walker embodiment 400 having a body 402 from which a posterior portion 406 pivots away relative to an anterior portion 404. The walker 400 provides a rear entry opening by the posterior portion 406 opening for ease of donning and doffing. The body 402 may be unitary with the anterior and posterior portions 404, 406, such that a living hinge 412 permits articulation by the posterior portion 406. The posterior portion 406 may overlap with a proximal anterior portion 410 and can fasten with a fastener 416. A strap 414 may be provided to circumferentially extend about the anterior and posterior portions 404, 406, and extend through a slot 418 formed by the posterior portion 406. The posterior portion 406 may comprise medial/lateral wings 408 that may extend around and overlap a portion of the anterior portion 410, such that as the strap 414 extends around the wings 408 and the anterior portion 410, an improved fit may be achieved.

Figure 16A:
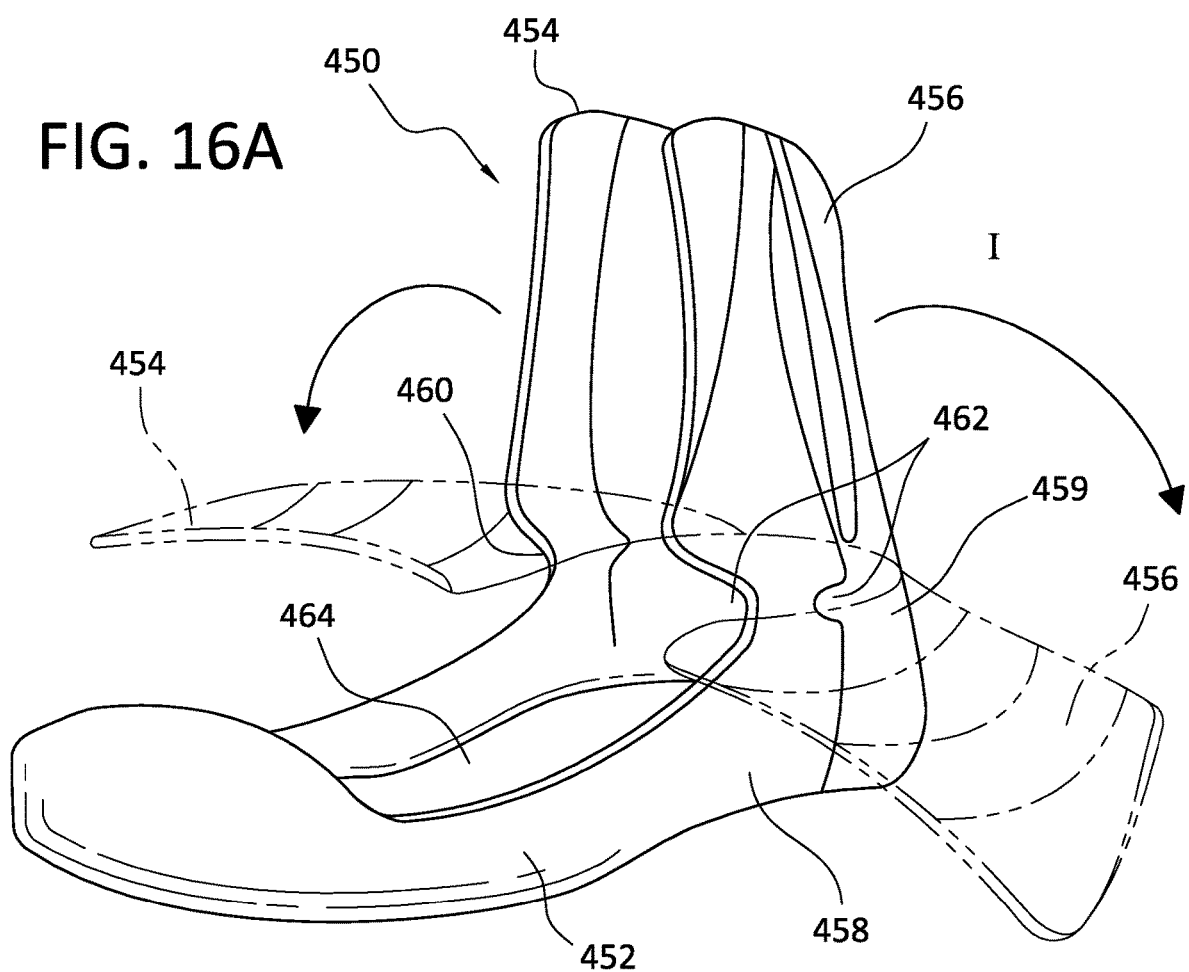
FIG. 16A is a schematic perspective view of another embodiment of an orthopedic walker in first and second configurations (I, II).

FIG. 16A illustrates an embodiment of a walker 450 with a body 452 having first and second portions 454, 456 forming struts to the walker 450, yet arranged to open by biasing about living hinges 458 formed from the body 452. The first and second portions 454, 456 may be trimmable to accommodate the specific dimensions of a user. The first and second portions 454, 456 may comprise individual sections 159 that are arranged to be discretized and separated from adjacent sections of the first and second portions 454, 456 to form struts of a user-tailored length. Recesses or relief areas 464 may be defined on opposed sides, for example anterior and posterior sides, of a flex portion 460, to reduce material and facilitate outward and inward biasing of the first and second portions 454, 456. A footbed 464 may comprise any suitable material for supporting a user, including added components such as Achilles tendon wedges, memory foam, shock absorbing material, heat-formable materials, or any other suitable material.

Figure 16B:
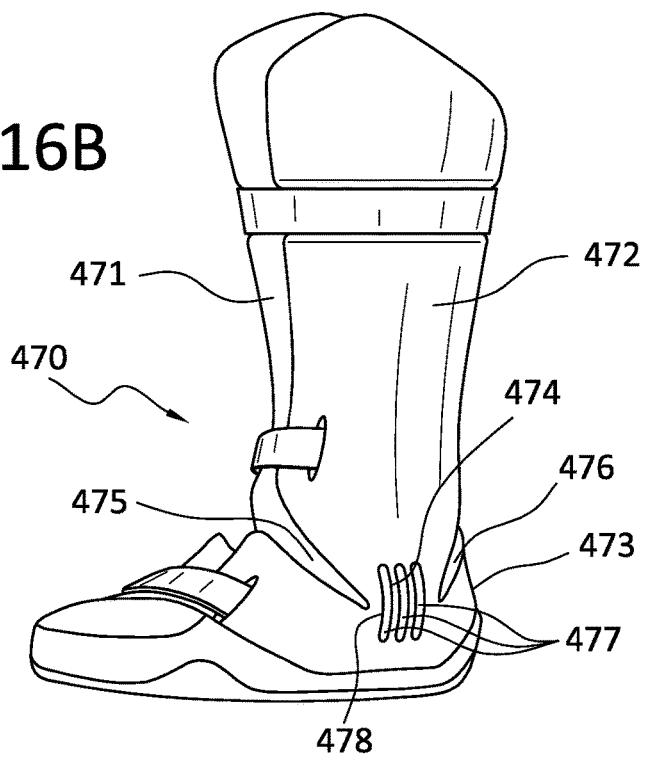
FIG. 16B is a side elevational view of another embodiment of an orthopedic walker having a hinge feature.

FIG. 16B shows another embodiment of an orthopedic walker 470 having a hinge feature 474 about an articulating portion 478 of the walker 470 to facilitate first and second portions 471, 472 to open and close for donning generally along a median plane of the orthopedic walker 470. The first and second sides corresponding to the first and second portions 471, 472 may have similar structure to enable each to articulate. Relief areas 475, 476 may be provided on anterior and posterior sides of the first and second portions 471, 472 to reduce material at or about the articulating portion 478. At least one material relief segment 477 may be provided within the articulating portion 478 to better enable each of the first and second portions 471, 472 to articulate relative to one another.

Figure 17C:
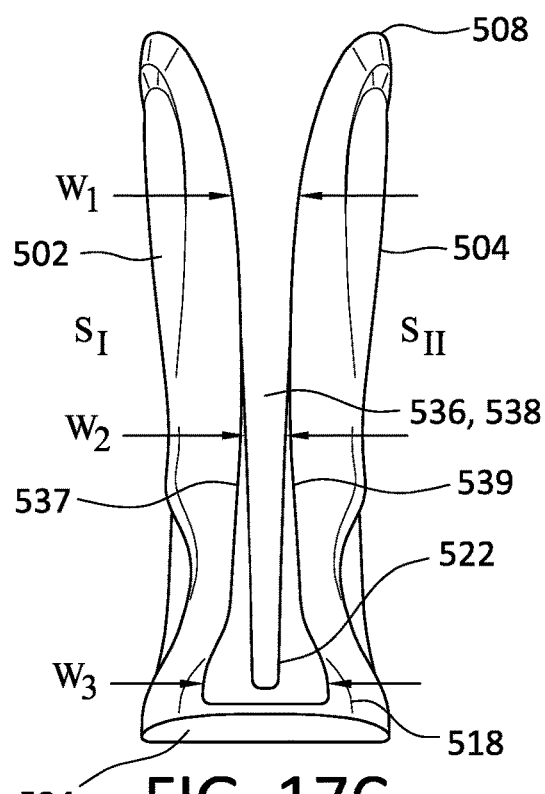
FIG. 17C is a front elevational view of the orthopedic walker of FIG. 17A.
Figure 17D:
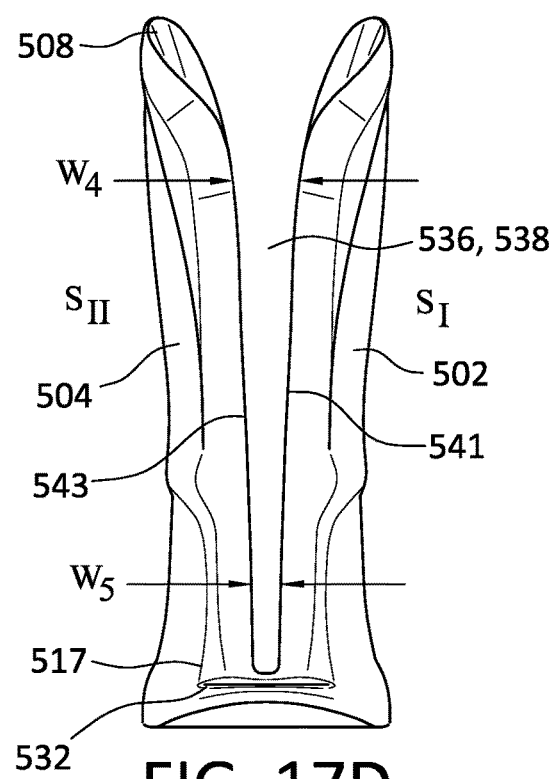
FIG. 17D is a rear elevational view of the orthopedic walker of FIG. 17A.
Figure 17E:
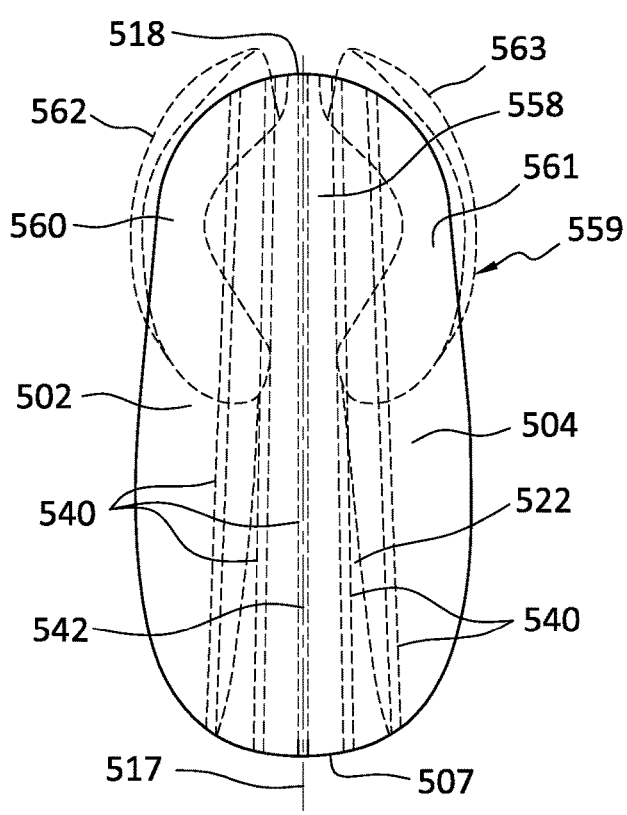
FIG. 17E is a top plan view of the orthopedic walker of FIG. 17A.
Figure 17F:
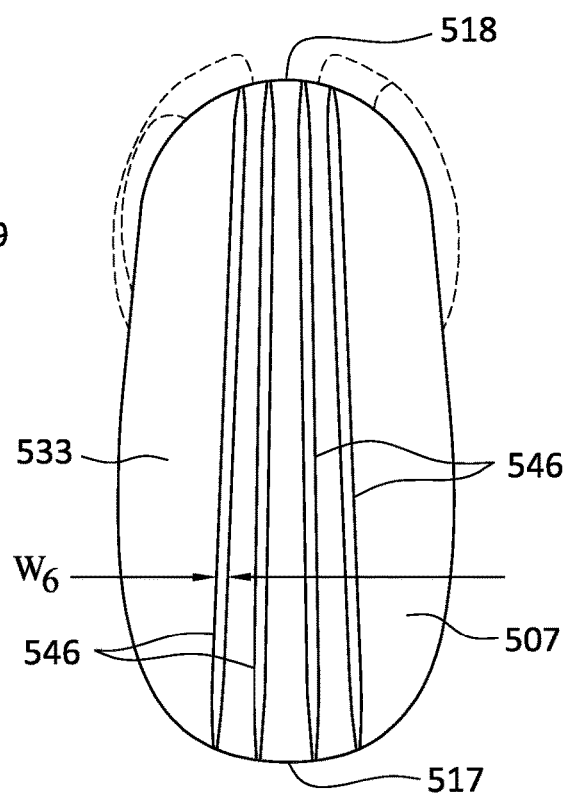
FIG. 17F is a bottom plan view of the orthopedic walker of FIG. 17A.
Figure 17G:
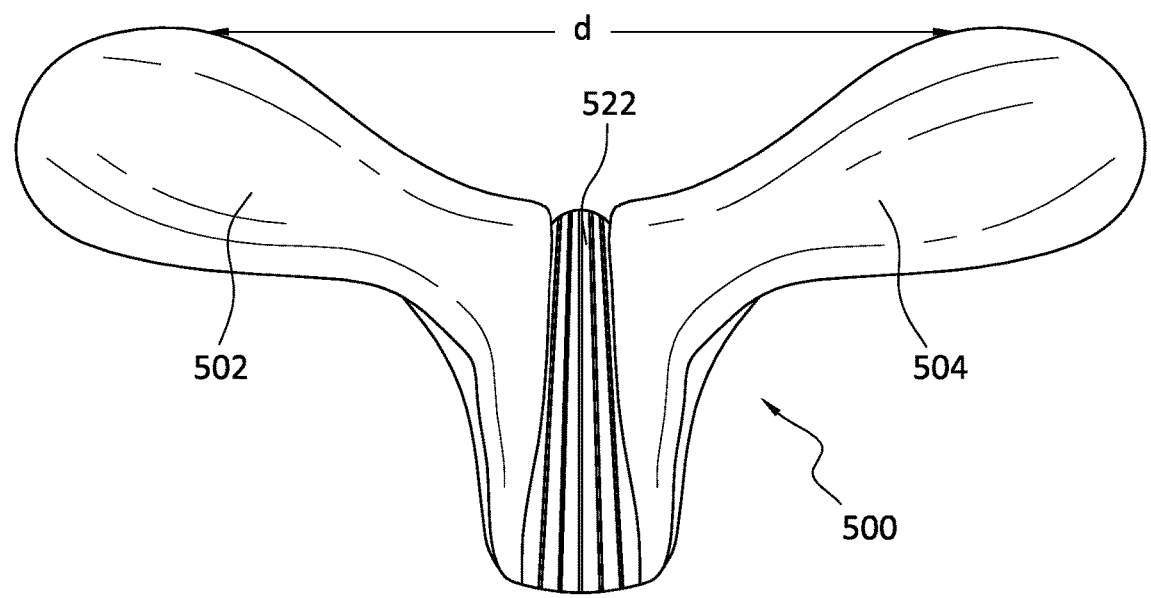
FIG. 17G is a schematic view showing the orthopedic walker of FIG. 17A having first and second portion articulating individually relative to one another.
Figure 17H:
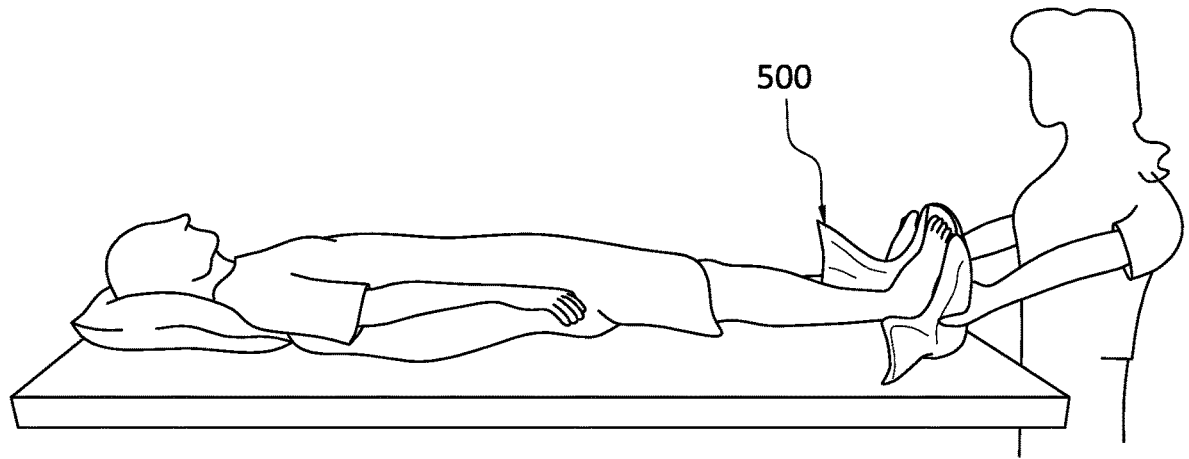
FIG. 17H is a schematic view exemplifying donning the orthopedic walker of FIG. 17A when a user is in a supine position.
Figure 18A:
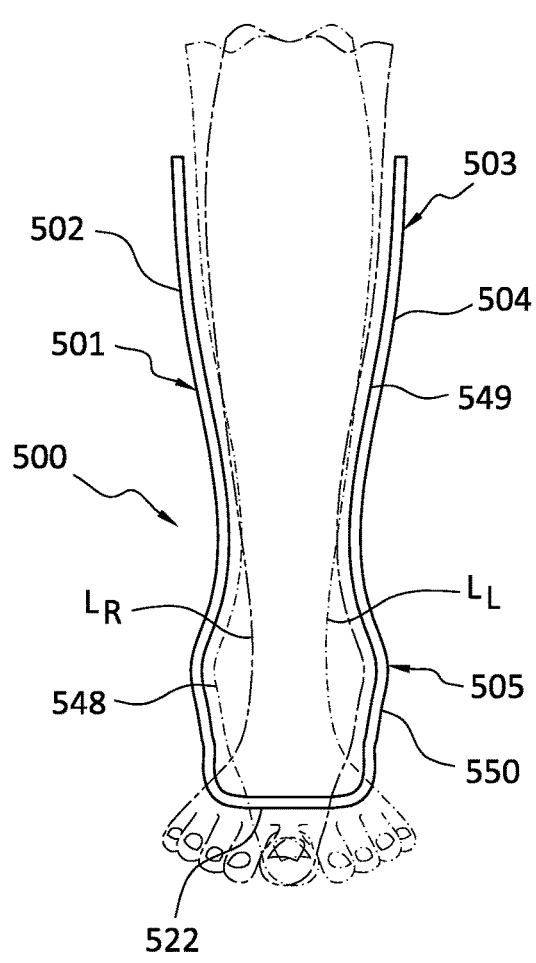
FIG. 18A is a schematic view showing an anterior side of an orthopedic walker according to a variation and arranged for universal use.

FIGS. 17A-17H and FIGS. 18A-B illustrate another embodiment of an orthopedic walker 500 arranged for universal use for both right and left legs and feet. The walker 500 has generally symmetrical first and second sides $S_I$, $S_{II}$, divided by the median plane $M_p$. FIG. 18A shows how first and second portions 502, 504 are symmetrical relative to one another so they can accommodate both right and left legs and feet, although they each have a curvilinear profile 548 from proximal to distal ends. The curvilinear profile 548 is defined to more naturally fit a leg, ankle and foot, as compared to conventional walkers. The spacing of the first and second portions 502, 504 taper through the upper receiving section 503, and are contoured to accommodate the malleolus of an ankle in at least the lower receiving section 505.

For example, the curvilinear profile 548 may define an expanded portion 550 proximate the malleolus for accommodating and comfortably immobilizing a user's leg, while defining a different width along the leg at tapering profile 549. In embodiments, the walker 500 may accommodate leg profiles $L_L$ corresponding to a left leg and $L_R$ corresponding to a right leg, thus simplifying the process of providing an appropriate support to a user. The footbed 522 may be contoured accordingly to accommodate both right and leg feet. In embodiments, the first and second sides $S_I$, $S_{II}$ may define a same profile by being symmetrical such that the fit for right and left legs is the same.

Figure 18B:
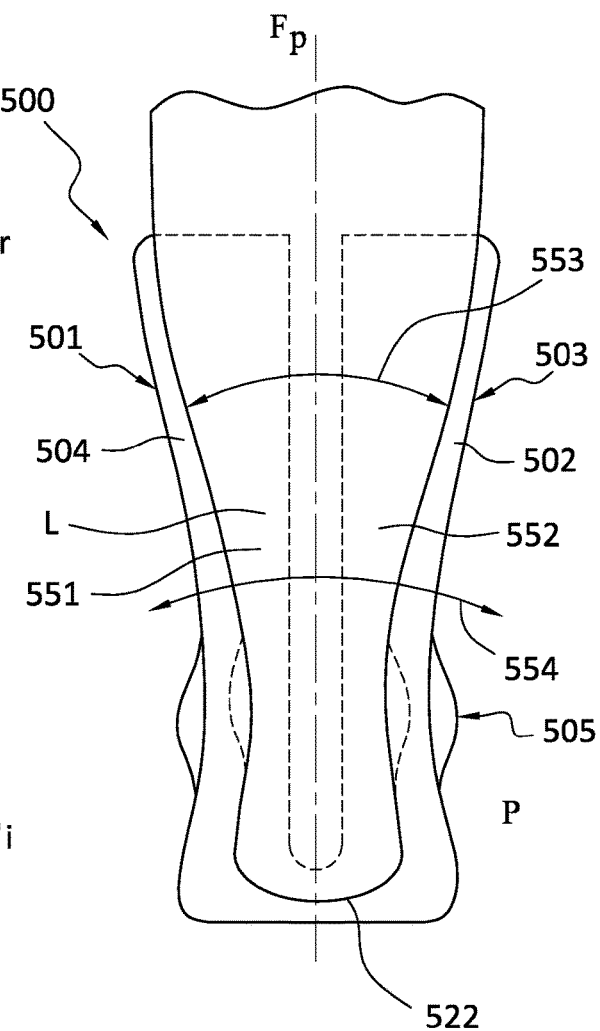
FIG. 18B is a schematic view showing the posterior side of the orthopedic walker of FIG. 18A.

FIG. 18B illustrates how the walker 500 has improved frontal plane control along the frontal plane Fp, particularly in view of conventional double strut walkers. The improved frontal plane Fp control is achieved by the first and second portions of at least the upper and lower receiving sections 503, 505 having extending regions 551, 552 wrapping about the anterior and posterior sides of a user's leg, such that when straps 553, 554 are provided about the first and second portions 502, 504, the walker 500 is better able arrest or immobilize the leg. The extending regions 551, 553 are provided without adversely increasing the weight of the walker 500 since when an expanded thermoplastic is used to form the walker body 501, significant weight savings are achieved.

In an alternative embodiment, a profile defined on a medial and a lateral side of the walker 500 may not be symmetrical but may rather be side-specific; that is, portions may be fitted to the dimensions common in a left or a right leg. Portions proximate the calf and the malleolus, for example, may be adjusted to accommodate a side-specific dimension, with the malleolus portion on a medial side arranged to be higher and more anterior, for example, or to be more profile if less space is needed to make the walker 500 universal, as a universal walker requires more space to accommodate either malleolus. Additionally, a side-specific walker 500 may have a narrower and asymmetrically shaped footbed 507, with a narrower toe portion to improve roll-over/gait dynamics late in the stance phase.

Returning to the embodiment of FIGS. 17A-17H, the walker 500 defines a body 501 formed from at least one polymeric material. The body 501 defines an upper receiving section 503, a lower receiving section 505, and a footbed 507. The upper receiving section 503 includes first and second portions 502, 504 divided by a median plane of the orthopedic walker $M_p$.

As depicted in FIG. 17G, the first and second portions 502, 504 are arranged to individually articulate or pivot (from generally at the lower receiving portion and/or footbed) about or from the median plane $M_p$ to expand or retract a variable distance d between the first and second portions 502, 504. The variable distance d may increase as the first and second portions 502, 504 pivot or articulate by being able to extend from an upright predetermined configuration to at least pivoting 90 degrees or at least perpendicularly to an open configuration. The upright predetermined configuration is a default position in which the first and second portions 502, 504 rest or return to if a load to pivot the first and second portions is outwardly released.

The upright predetermined configuration is achieved by at least resiliency of the polymeric material forming the first and second portions 502, 504, and/or or the structural shape and configuration of the first and second portions 502, 504 relative to the lower receiving section 505 and/or footbed 507. The upright predetermined configuration generally is oriented so the first and second portions 502, 504 extend in the proximal $P_r$ and distal $D_r$ directions and is a default configuration. Although the first and second portions 502, 504 can pivot outwardly at least perpendicularly away from each other to open the walker 500 for donning, the first and second portions 502, 504 may pivot inwardly toward one another upon application of a load, such as using a strap to tension at least in a circumferential or partially circumferential orientation about the walker 500.

By individually articulating, each of the first and second portions 502, 504 can be pivoted or articulated distally from a predetermined configuration without necessarily moving the other one of the first and second portions 502, 504. Likewise, the first and second portions 502, 504 can be arranged so they both open simultaneously opening or tilting toward the distal end of the body 501 to enable quick and simple donning.

FIG. 17H shows how the walker 500 can be donned when the user is in a supine position. Often the protocol is to maintain the user in a supine position after surgery, and the arrangement of opening the walker 500 enables the walker 500 to be donned without lifting the leg and foot. However, the user need not be in a supine position to don the walker 500 and may be donned by the user opening and/or stepping into the walker 500.

FIGS. 17E and 17F exemplify how the walker 500 need not merely rely on the resiliency of material forming the body 501 to permit articulation. The footbed 507 may include at least one channel or groove 540, 542 located along and into a thickness of the inner surface 522 between anterior and posterior ends 517, 518. A central groove 542 extends generally along the median plane $M_p$ to allow the articulation of the walker 500 to occur at the footbed 507 rather than merely pivoting the first and second portions 502, 504, either by resiliency of the material forming the walker 500 and/or with a hinge.

Additional grooves 542 may be provided alongside the central groove 542 to allow the footbed 507 to fan or bend to achieve the supine donning of the walker 500, as depicted in FIG. 17G. The footbed 507 may have a special shape or configuration to address and minimize rollover.

Because of the material used to form the footbed 507, such as an expanded thermoplastic like EVA, the footbed 507 may advantageously attain a same comfort level as existing devices yet have a reduced build height relative to existing devices as special insole material may be omitted without sacrificing comfort. In existing walkers, hard plastics are used to create immobilization of the limb, with a certain thickness for optimal immobilization. Thick foam soles are added to provide cushioning against the hard-plastic body to improve comfort in gait. Because of the improved rollover-prevention profile and the EVA, the thick foam soles in combination with the hard-plastic layer of conventional devices may be reduced and/or removed.

The outer surface 534 of the footbed 507 may likewise form at least one groove 546 generally along or alongside the median plane $M_p$. Either of the grooves of the inner surface 522 or outer surface 534 may have grooves with a uniform width or a variable width according to a location relative to the anterior and posterior ends 517, 518. Although the grooves are shown as extending a length of the footplate between the anterior and posterior ends 517, 518, they may extend only partially and/or in different directions, patterns, and/or spacings.

The body 501 defines at least two openings 536, 538 at least partially separating the upper receiving section 503 of the body 501 into the first and second portions 502, 504. As The at least two openings 536, 538 are preferably opposite one another generally along the median plane $M_p$, and generally extending elongate in the proximal $P_r$ and distal $D_r$ directions. Although the at least two openings 536, 538 can articulate relative to one another, the first and second portions 502, 504 may be variably spaced relative to one another in a predetermined configuration, without intentionally varying the distance of the first and second portions 502, 504 relative to one another. FIG. 17C shows how first and second anterior edges 537, 539 may be spaced at a width $w_1$ at a proximal end of the body 501, whereas at a middle location the width $w_2$ may be less than at width w1. The first and second anterior edges 537, 539 at the footbed or distal end may be spaced wider with a width $w_3$ than the width w2.

Similarly, first and second posterior edges 541, 543 of the first and second portions 502, 504 may be spaced variably relative to one another, whereby a proximal portion may have a width $w_4$ and a distal portion may have width $w_5$. The spacing of the at least two elongate openings 536, 538 may be different relative to one another, and may vary in the proximal $P_r$ and distal $D_r$ directions differently according to the unique anatomy of a leg, ankle and foot generally on the anterior and posterior sides, and lateral and medial sides.

As shown, the body 501 consists the upper receiving section 503, the lower receiving section 505, and the footbed 507 as a continuous structure formed unitarily from the at least one polymeric material. According to a preferred embodiment, the at least one polymeric material may be an expanded thermoplastic, which offers weight savings while offering a rigid structure. Although not limited, according to a preferred embodiment, the expanded thermoplastic may be selected from the group consisting of polyurethane, polyethylene, polypropylene and ethylene-vinyl acetate.

According to the preferred embodiment, the first and second portions 502, 504 are symmetrical relative to one another, such that the first and second portions have a curvilinear profile extending between and among the proximal $P_r$ and distal $D_r$ directions of the upper receiving section 504. The first and second portions 502, 504 have a convex profile 560, 561 along an inner surface 558 thereof. The first and second portions 502, 504 have convex profiles 562, 563 along an outer surface 559 thereof generally corresponding to the concavity of the inner surface 558, as it is intended that the convex profile 560, 561 closely contours to the leg and ankle in the walker 500, particularly if the first and second portions 502, 504 pivot to accommodate a user's leg once or as the walker 500 is donned.

The upper receiving section 503 may have a varying wall thickness, or a substantially uniform wall thickness, as explained in relation to foregoing embodiments. The upper receiving section 503 may have an increased thickness at least proximate a periphery 508 thereof relative to areas outside the periphery 506. The increased thickness may have a tapering width 510 in sections and may connect with regions having curvilinear thickness differences 512 according to areas requiring additional support, than at areas such as areas 506, 514, 516 outside of the increased thickness. The areas requiring additional support may be at the ankle to better immobilize movement in the frontal plane, or at an anterior toe area 518.

As shown in FIG. 17B, the reinforcing area 512 extends above the malleolus 545 with anterior and posterior sections 524, 528 gradually extending to a crest 526 to form a transitional support more proximate to a user's anatomy and regions by which the user may require enhanced frontal plane control. The reinforcing area 512 may only protrude outwardly without interfering with the inner side of the 558 body, which interfaces with the user's leg, ankle and foot.

The footbed 507 may have a substantially decreased thickness t over conventional walkers, as shown with the anterior lip 530. A problem often occurs with a mismatch of height of the walker compared to the unaffected foot, ankle and leg. The footbed 507 has an inner surface 522 upon which the foot is placed and extends a length 520 of the distal end portion of the walker. The improved support by the upper and lower receiving portions 503, 505 enables a thinner footbed 507, coupled with the unitary construction of the body 501 of the walker 500. An outer surface 534 of the footbed 534 may have a curvilinear profile 535 with a tread (not shown) to enable foot rollover and traction for walking.

Referring in part to FIG. 11C and FIG. 17B, the footbed 507 may include the lip 530 and a posterior groove 532 for at least interlocking with a sole component.

By providing an orthopedic walker according to embodiments of the disclosure, an orthopedic walker may combine the benefits of existing casting devices and existing orthopedic braces in a walker that is both lightweight compared to existing devices and nevertheless comprises necessary strength and rigidity for immobilization and support of a limb of a user.

Orthopedic walkers according to the embodiments may comprise additional features for supporting a limb of a user without adding significant weight, such as stays or inserts, ventilation openings, longitudinal openings facilitating supine donning and doffing, removable outer soles, and others.

It is to be understood that not necessarily all objects or advantages may be achieved under any embodiment of the disclosure. Those skilled in the art will recognize that an orthopedic walker may be embodied or carried out in a manner that achieves or optimizes one advantage or group of advantages as taught herein without achieving other objects or advantages as taught or suggested herein.

The skilled artisan will recognize the interchangeability of various disclosed features. Besides the variations described herein, other known equivalents for each feature can be mixed and matched by one of ordinary skill in this art to build and use an orthopedic device under principles of the present disclosure. It will be understood by the skilled artisan that the features described herein may be adapted to other methods and types of orthopedic and prosthetic devices.

Although this disclosure describes certain exemplary embodiments and examples of an orthopedic walker, it will be understood by those skilled in the art that the present disclosure extends beyond the specifically disclosed patellofemoral support to other alternative embodiments and/or uses of the disclosure and obvious modifications and equivalents thereof, including other types and components of orthopedic, prosthetic, and medical devices. It is intended that the present disclosure should not be limited by the disclosed embodiments described above and may be extended to other applications that may employ the features described herein.

The invention claimed is:

1. An orthopedic walker consisting essentially of:
    a body having a unitary construction consisting a single expanded thermoplastic material defined as a closed-cell foam, wherein the body defines exterior and interior surfaces with a variable thickness therebetween such that the expanded thermoplastic material spans the variable thickness between the exterior and interior surfaces;
    the body defining an upper receiving section, a lower receiving section, and a footbed;
    wherein the upper receiving section includes first and second portions divided by a median plane of the orthopedic walker, the first and second portions and the lower receiving section adjacent to the first and second portions are arranged to articulate about or from the median plane to expand or retract a variable distance between the first and second portions of the upper receiving section;
    wherein the first and second portions have opposing arcuate cross-sections along and between proximal and distal portions of the upper receiving section and extend in posterior and anterior directions toward the median plane, the first and second portions being configured and dimensioned to enclose a lower leg of a user;
    wherein the first and second portions are configured to expand the upper receiving section into an opened state to receive the lower leg of the user and to retract the upper receiving section into a closed state to enclose the lower leg of the user;
    wherein the first and second portions of the upper receiving section are biased toward the closed state by at least resiliency of the expanded thermoplastic material, such that the first and second portions return to the closed state as a load to pivot the first and second portions about or from the median plane is outwardly released;
    wherein the body consists of the upper receiving section, the lower receiving section, and the footbed as a continuous structure formed unitarily from the expanded thermoplastic material;

wherein the body defines elongate anterior and posterior openings opposite one another along the median plane of the body spacing the first and second portions apart from one another along both posterior and anterior sides;

wherein the elongate posterior opening extends from a proximal end of the upper receiving section to a posterior end of the footbed and the elongate anterior opening extends from a proximal end of the upper receiving section to an anterior end of the footbed, the elongate anterior and posterior openings being separate from one another.

2. The orthopedic walker according to claim 1, wherein the first and second portions have a same profile such that the upper receiving section is arranged for both right and left legs of the user.

3. The orthopedic walker according to claim 2, wherein each of the first and second portions has a curvilinear profile extending between and among proximal and distal portions of the upper receiving section, and the first and second portions have a convex profile along an inner surface thereof.

4. The orthopedic walker according to claim 3, wherein the first and second portions have convex profiles along an outer surface thereof corresponding to the convex profile of the inner surface.

5. The orthopedic walker according to claim 1, wherein the footbed includes at least one elongate groove extending along or parallel to the median plane of the orthopedic walker.

6. The orthopedic walker according to claim 5, wherein the at least one elongate groove extends along either an inner surface or an outer surface of the footbed and extending a thickness into the footbed.

7. The orthopedic walker according to claim 1, wherein the elongate posterior opening tapers in width from the proximal end to a distal end of the upper receiving section.

8. The orthopedic walker according to claim 1, wherein the elongate anterior opening widens from a proximal end to a distal end of the lower receiving section.

9. The orthopedic walker according to claim 1, wherein the elongate anterior opening extends along an entirety of the body on an anterior side of the body from the upper receiving section to the lower receiving section.

10. The orthopedic walker according to claim 1, wherein the upper receiving section has a varying wall thickness.

11. The orthopedic walker according to claim 1, wherein the lower receiving section includes first and second sides defined by the median plane, the first and second sides having a same profile such that the lower receiving section is arranged for both right and left feet of the user.

12. The orthopedic walker according to claim 1, wherein the body is arranged to exhibit an increasing rigidity from a proximal end to a distal end.

13. The orthopedic walker according to claim 1, wherein the body defines a curvilinear reinforcement feature dividing the upper receiving section from the lower receiving section, the curvilinear reinforcement feature defining greater rigidity of the body than areas of the body adjacent thereto.

14. The orthopedic walker according to claim 1, wherein the single expanded thermoplastic material is selected from a group consisting of polyurethane, polyethylene, polypropylene and ethylene-vinyl acetate.

15. The orthopedic walker according to claim 1, wherein the footbed defines a sole on the exterior surface having treads.

16. An orthopedic walker consisting essentially of:
a body formed from a single expanded thermoplastic material having a closed-cell foam structure;
the body defining an upper receiving section, a lower receiving section, and a footbed;
wherein the body defines posterior and anterior openings, the posterior and anterior openings separating the upper receiving section of the body into a first portion and a second portion on opposite sides of a median plane of the orthopedic walker, the posterior and anterior openings being opposite one another along the median plane of the orthopedic walker, the posterior opening terminating above the footbed;
wherein the first and second portions having a same profile such that the upper receiving section is arranged for both right and left legs of a user;
wherein the first and second portions are configured to expand the upper receiving section into an opened state to receive the lower leg of the user and to retract the upper receiving section into a closed state to enclose the lower leg of the user;
wherein the first and second portions of the upper receiving section are biased toward the closed state by at least resiliency of the expanded thermoplastic material, such that the first and second portions return to the closed state as a load to pivot the first and second portions about or from the median plane is outwardly released;
wherein the first and second portions and the lower receiving section adjacent to the first and second portions are arranged to individually articulate about or from the median plane to expand or retract a variable distance between the first and second portions of the upper receiving section along one of anterior or posterior sides of the body;
wherein the footbed includes at least one elongate groove extending along or parallel to the median plane of the orthopedic walker, the at least one elongate groove extending a thickness into the footbed;
wherein the single expanded thermoplastic material is selected from a group consisting of polyurethane, polyethylene, polypropylene and ethylene-vinyl acetate.

17. The orthopedic walker according to claim 16, wherein the footbed defines a sole on the exterior surface having treads.

18. The orthopedic walker according to claim 16, wherein the at least one elongate groove extends along either an inner surface or an outer surface of the footbed.

19. The orthopedic walker according to claim 16, wherein the first and second portions have opposing arcuate cross-sections along and between proximal and distal portions of the upper receiving section and extend in posterior and anterior directions toward the median plane, the first and second portions being configured and dimensioned to enclose a lower leg of the user.

20. An orthopedic walker consisting essentially of:
a body formed from a single expanded thermoplastic consisting of ethylene-vinyl acetate, the expanded thermoplastic having a closed-cell foam structure;
the body defining an upper receiving section, a lower receiving section, and a footbed;
wherein the body consists of the upper receiving section, the lower receiving section, and the footbed as a continuous structure formed unitarily from the expanded thermoplastic;
wherein the upper receiving section includes first and second portions divided by a median plane of the orthopedic walker, the first and second portions and the lower receiving section adjacent to the first and second portions are arranged to articulate about or from the median plane to expand or retract a variable distance between the first and second portions of the upper receiving section;

wherein the first and second portions have opposing arcuate cross-sections along and between proximal and distal portions of the upper receiving section and extend in posterior and anterior directions toward the median plane, the first and second portions being configured and dimensioned to enclose a lower leg of a user;

wherein the first and second portions are configured to expand the upper receiving section into an opened state to receive the lower leg of the user and to retract the upper receiving section into a closed state to enclose the lower leg of the user;

wherein the first and second portions of the upper receiving section are biased toward the closed state by at least resiliency of the expanded thermoplastic material, such that the first and second portions return to the closed state as a load to pivot the first and second portions about or from the median plane is outwardly released;

wherein the first and second portions have a same profile such that the upper receiving section is arranged for both right and left legs of the user, the first and second portions each having a curvilinear profile along anterior and posterior sides of the body;

wherein the body defines elongate anterior and posterior openings opposite one another along the median plane of the body spacing the first and second portions apart from one another along both posterior and anterior sides;

wherein the elongate posterior opening extends from a proximal end of the upper receiving section to a posterior end of the footbed and the elongate anterior opening extends from a proximal end of the upper receiving section to an anterior end of the footbed, the elongate anterior and posterior openings being separate from one another;

wherein each of the first and second portions has the curvilinear profile extending between and among proximal and distal portions of the upper receiving section, and the first and second portions have a convex profile along an inner surface thereof, wherein the footbed defines a sole on an exterior surface having treads.

* * * * *